(12) United States Patent
Jantz et al.

(10) Patent No.: US 9,683,257 B2
(45) Date of Patent: Jun. 20, 2017

(54) RECOGNITION SEQUENCES FOR I-CREI-DERIVED MEGANUCLEASES AND USES THEREOF

(71) Applicant: Precision BioSciences, Inc., Durham, NC (US)

(72) Inventors: Derek Jantz, Durham, NC (US); James Jefferson Smith, Durham, NC (US)

(73) Assignee: Precision BioSciences, Inc., Durham, NC (US)

( * ) Notice: Subject to any disclaimer, the term of this patent is extended or adjusted under 35 U.S.C. 154(b) by 70 days.

(21) Appl. No.: 14/315,676

(22) Filed: Jun. 26, 2014

(65) Prior Publication Data

US 2015/0050655 A1    Feb. 19, 2015

Related U.S. Application Data

(63) Continuation of application No. 13/006,625, filed on Jan. 14, 2011, now abandoned, which is a continuation of application No. PCT/US2009/050566, filed on Jul. 14, 2009.

(60) Provisional application No. 61/080,453, filed on Jul. 14, 2008.

(51) Int. Cl.
    *C12N 9/22* (2006.01)
    *G06Q 99/00* (2006.01)
    *C12Q 1/68* (2006.01)

(52) U.S. Cl.
    CPC .............. *C12Q 1/6811* (2013.01); *C12N 9/22* (2013.01); *G06Q 99/00* (2013.01)

(58) Field of Classification Search
    None
    See application file for complete search history.

(56) References Cited

U.S. PATENT DOCUMENTS

| | | |
|---|---|---|
| 5,436,150 A | 7/1995 | Chandrasegaran |
| 5,474,896 A | 12/1995 | Dujon et al. |
| 5,789,215 A | 8/1998 | Berns et al. |
| 5,792,632 A | 8/1998 | Dujon et al. |
| 5,792,640 A | 8/1998 | Chandrasegaran |
| 5,830,729 A | 11/1998 | Jaisser et al. |
| 5,866,361 A | 2/1999 | Dujon et al. |
| 5,948,678 A | 9/1999 | Dujon et al. |
| 5,962,327 A | 10/1999 | Dujon et al. |
| 6,238,924 B1 | 5/2001 | Dujon et al. |
| 6,265,196 B1 | 7/2001 | Chandrasegaran |
| 6,395,959 B1 | 5/2002 | Dujon et al. |
| 6,566,579 B1 | 5/2003 | Jaisser et al. |
| 6,610,545 B2 | 8/2003 | Dujon et al. |
| 6,794,136 B1 | 9/2004 | Eisenberg et al. |
| 6,822,137 B1 | 11/2004 | Dujon et al. |
| 6,833,252 B1 | 12/2004 | Dujon et al. |
| 7,214,536 B2 | 5/2007 | Dujon et al. |
| 7,271,000 B2 | 9/2007 | Dujon et al. |
| 7,309,605 B1 | 12/2007 | Dujon et al. |
| 8,021,867 B2 | 9/2011 | Smith et al. |
| 2002/0107214 A1 | 8/2002 | Choulika et al. |
| 2002/0110898 A1 | 8/2002 | Choulika et al. |
| 2003/0113887 A1 | 6/2003 | Dujon et al. |
| 2003/0175968 A1 | 9/2003 | Golic et al. |
| 2003/0182670 A1 | 9/2003 | Dujon et al. |
| 2003/0229039 A1 | 12/2003 | Choulika et al. |
| 2004/0002092 A1 | 1/2004 | Arnould et al. |
| 2004/0019002 A1 | 1/2004 | Choulika et al. |
| 2004/0068761 A1 | 4/2004 | Golic et al. |
| 2004/0171154 A1 | 9/2004 | Storici et al. |
| 2005/0026157 A1 | 2/2005 | Baltimore et al. |
| 2005/0032223 A1 | 2/2005 | Dujon et al. |
| 2005/0064474 A1 | 3/2005 | Urnov et al. |
| 2005/0172365 A1 | 8/2005 | Puchta et al. |
| 2005/0208489 A1 | 9/2005 | Carroll et al. |
| 2006/0078552 A1 | 4/2006 | Arnould et al. |
| 2006/0153826 A1 | 7/2006 | Arnould et al. |
| 2006/0206949 A1 | 9/2006 | Arnould et al. |
| 2006/0282914 A1 | 12/2006 | D'Halluin et al. |
| 2007/0117128 A1 | 5/2007 | Smith et al. |

FOREIGN PATENT DOCUMENTS

| | | |
|---|---|---|
| EP | 1485475 | 12/2004 |
| WO | WO-96/14408 | 5/1996 |
| WO | WO-0046386 A3 | 8/2000 |
| WO | WO-03078619 A1 | 9/2003 |
| WO | WO-2004031346 A2 | 4/2004 |
| WO | WO-2004/067736 A2 | 8/2004 |
| WO | WO-2004067753 A2 | 8/2004 |
| WO | WO-2005049842 A2 | 6/2005 |

(Continued)

OTHER PUBLICATIONS

Aagaard, C. et al., "Profile of the DNA recognition site of the archaeal homing endonuclease I-Dmol," Nucleic Acids Res., vol. 25. No. 8, pp. 1523-1530 (Apr. 15, 1997).

Aggarwal, A. K. and Wah, D., "Novel site-specific DNA endonucleases," Current Opinion in Structural Biology, vol. 8, No. 1, pp. 19-25 (Feb. 1998).

Argast, G. M. et al., "I-Ppol and I-Crel homing site sequence degeneracy determined by random mutagenesis and sequential in vitro enrichment," J. Mol. Biol., vol. 280, No. 3, pp. 345-353 (Jul. 17, 1998).

Arnould, S. et al. "Engineered I-Crel Derivatives Cleaving Sequences from the Human XPC Gene Can Induce Highly Efficient Gene Correction in Mammalian Cells." J. Mol. Biol., vol. 371, No. 1, pp. 49-65 (Aug. 3, 2007).

Arnould, S. et al., "Engineering of large numbers of highly specific homing endonucleases that induce recombination of novel DNA targets," J. Mol. Biol., vol. 355, No. 3, pp. 443-458 (Jan. 20, 2006).

(Continued)

*Primary Examiner* — Suzanne M Noakes
*Assistant Examiner* — Jae W Lee
(74) *Attorney, Agent, or Firm* — Wilmer Cutler Pickering Hale and Dorr LLP

(57) ABSTRACT

Methods of cleaving double-stranded DNA that can be recognized and cleaved by a rationally-designed, I-CreI-derived meganuclease are provided. Also provided are recombinant nucleic acids, cells, and organisms containing such recombinant nucleic acids, as well as cells and organisms produced using such meganucleases. Also provided are methods of conducting a custom-designed, I-CreI-derived meganuclease business.

10 Claims, 5 Drawing Sheets

(56) References Cited

FOREIGN PATENT DOCUMENTS

| WO | WO-2005105989 A1 | 11/2005 |
|---|---|---|
| WO | WO-2006097784 A1 | 9/2006 |
| WO | WO-2006097853 A1 | 9/2006 |
| WO | WO-2006097854 A1 | 9/2006 |
| WO | WO-2007034262 A1 | 3/2007 |
| WO | WO-2007047859 A2 | 4/2007 |
| WO | WO-2007049095 A1 | 5/2007 |
| WO | WO-2007049156 A2 | 5/2007 |
| WO | WO-2007057781 A3 | 5/2007 |
| WO | WO-2007060495 A1 | 5/2007 |
| WO | WO-2007093836 A1 | 8/2007 |
| WO | WO-2007093918 A2 | 8/2007 |
| WO | WO-2008010009 A1 | 1/2008 |
| WO | WO-2008010093 A2 | 1/2008 |
| WO | WO-2008059317 A1 | 5/2008 |
| WO | WO-2008093152 A1 | 8/2008 |
| WO | WO-2008093249 A2 | 8/2008 |
| WO | WO-2008102198 A1 | 8/2008 |
| WO | WO-2008102199 A1 | 8/2008 |
| WO | WO-2008102274 A2 | 8/2008 |
| WO | WO-2008149176 A1 | 12/2008 |
| WO | WO-2008152523 A1 | 12/2008 |
| WO | WO-2009006297 A2 | 1/2009 |
| WO | WO-2009013559 A1 | 1/2009 |
| WO | WO-2009013622 A2 | 1/2009 |
| WO | WO-2009019528 A1 | 2/2009 |
| WO | WO-2009019614 A2 | 2/2009 |
| WO | WO-2010026443 A1 | 3/2010 |

OTHER PUBLICATIONS

Ashworth, J. et al., "Computational redesign of endonucleases DNA binding and cleavage specificity," Nature, vol. 441, pp. 656-659 (Jun. 1, 2006).
Australian Office Action issued by the Australian Government Patent Office for Patent Application No. 2009271011 dated Feb. 9, 2015 (4 pages).
Belfort, M. et al., "Homing enconucleases: keeping the house in order," Nucleic Acids Research, vol. 25, No. 17, pp. 3379-3388 (Jul. 18, 1997).
Beumer, K. et al., "Efficient gene targeting in *Drosophila* with zinc finger nucleases," Genetics, vol. 172, No. 4, pp. 2391-2403 (Feb. 1, 2006).
Bibikova, M. et al., "Enhancing gene targeting with designed zinc finger nucleases," Science, vol. 300, No. 5620, p. 764 (May 2, 2003).
Bibikova, M. et al., "Stimulation of homologous recombination through targeted cleavage by chimeric nucleases," Molecular and Cellular Biology, vol. 21, No. 1, pp. 289-297 (Jan. 2001).
Bibikova, M. et al., "Targeted chromosomal cleavage and mutagenesis in *Drosophila* using zinc-finger nucleases," Genetics, vol. 161, No. 3, pp. 1169-1175 (Jul. 2002).
Bolduc, J. M. et al., "Structural and biochemical analyses of DNA and RNA binding by a bifunctional homing endonuclease and group I intron splicing factor," Genes Dev., vol. 17, No. 23, pp. 2875-2888 (Dec. 1, 2003).
Cahill, D. et al., "Mechanisms of eukaryotic DNA double strand break repair," Front Biosci., vol. 11, pp. 1958-1976 (May 1, 2006).
Chames, P. et al., "In vivo selection of engineered homing endonucleases using double-strand break induced homologous recombination," Nucleic Acids Research, vol. 33, No. 20, e178, pp. 1-10 (Nov. 23, 2005).
Chen, Ridong, "Enzyme engineering: rational redesign versus directed evolution," Trends Biotechnol., vol. 19, No. 1, pp. 13-14 (Jan. 2001).
Chen, Z. and Zhao, H., "A highly sensitive selection method for directed evolution of homing endonucleases," Nucleic Acids Research, vol. 33, No. 18, e154, pp. 1-7 (Oct. 6, 2005).
Chevalier B. S. and Stoddard, B. L., "Homing Endonucleases: Structural and Functional Insight Into the Catalysts of Intron/Intein Mobility," Nucleic Acids Research, vol. 29, No. 18, pp. 3757-3774 (Sep. 15, 2001).
Chevalier, B. et al., "Flexible DNA target site recognition by divergent homing endoculease isoschizomers I-CreI and I-MsoI," J. Mol. Biol., vol. 329, No. 2, pp. 253-269 (May 30, 2003).
Chevalier, B. et al., "Metal-dependent DNA cleavage mechanism of the I-CreI LAGLIDADG homing endonuclease," Biochemistry, vol. 43, No. 44, pp. 14015-14026 (Nov. 9, 2004).
Chevalier, B. S. et al., "Design, activity, and structure of a highly specific artificial endonuclease," Molecular Cell, vol. 10, No. 4, pp. 895-905 (Oct. 2002).
Chevalier, B. S. et al., "The homing endonuclease I-CreI uses three metals, one of which is shared between the two active sites," Nature Structural Biology, vol. 8, No. 4, pp. 312-316 (Apr. 2001).
Chilton, M. D. and Que, Q., "Targeted integration of T-DNA into the tobacco genome at double-stranded breaks: new insights on the mechanism of T-DNA integration," Plant Physiology, vol. 133, No. 3, pp. 956-965 (Nov. 2003).
Cozzone, Alain J. "Proteins: Fundamental Chemical Properties," Encyclopedia of Life Sciences, John Wiley & Sons Ltd., pp. 1-10 (No Month Listed 2002).
Dalgaard, J. Z. et al. "A Site-Specific Endonuclease Encoded by a Typical Archaeal Intron," Proc. Natl. Acad. Sci. USA, vol. 90, No. 12, pp. 5414-5417 (Jun. 15, 1993).
Desjarlais, J. R. and Berg, J. M., "Use of a zinc-finger consensus sequence framework and specificity rules to design specific DNA binding proteins," Proc. Natl. Acad. Sci. USA, vol. 90, No. 6, pp. 2256-2260 (Mar. 15, 1993).
Dhanasekaran, M. et al., "Designer zinc finger proteins: tools for creating artificial DNA-binding functional proteins," Acc. Chem. Res., vol. 39, No. 1, pp. 45-52 (Jan. 2006).
Doyon, J. B. et al., "Directed evolution and substrate specificity profile of homing endonuclease I-SceI," J. Am. Chem. Soc., vol. 128, No. 7, pp. 2477-2484 (Feb. 22, 2006).
Duan, X. et al., "Crystal structure of PI-SceI, a homing endonuclease with protein splicing activity," Cell, vol. 89, No. 4, pp. 555-564 (May 16, 1997).
Durai, S. et al., "Zinc finger nucleases: custom-designed molecular scissors for genome engineering of plant and mammalian cells," Nucleic Acids Res., vol. 33, No. 18, pp. 5978-5990 (Oct. 26, 2005).
Epinat, J. C. et al., "A novel engineered meganuclease induces homologous recombination in yeast and mammalian cells," Nucleic Acids Research, vol. 31, No. 11, pp. 2952-2962 (Jun. 1, 2003).
European Office Action for European Patent Application No. 06 826 293.0 dated Nov. 20, 2008 (3 pages).
European Search Report for European Patent Application No. 10191885.2 mailed Apr. 26, 2011 (12 pages).
European Search Report for European Patent Application No. 10191888.6 mailed May 18, 2011 (5 pages).
European Search Report for European Patent Application No. 10191904.1 mailed May 13, 2011 (9 pages).
Fitzsimons Hall, M. et al., "Creation of an artificial bifunctional intein by grafting a homing endonuclease into a mini-intein," J. Mol. Biol., vol. 323, No. 2, pp. 173-179 (Oct. 18, 2002).
Gimble, F. S. et al., "Assessing the plasticity of DNA target site recognition of the PI-SceI homing endonuclease using a bacterial two-hybrid selection system," J. Mol. Biol., vol. 334, No. 5, pp. 993-1008 (Dec. 12, 2003).
Gimble, Frederick S., "Engineering Homing Endonulceases for Genomic Applications," Homing Endonucleases and Inteins, 16 pages (No month listed 2005).
Gouble, A. et al. "Efficient *in toto* Targeted Recombination in Mouse Liver by Meganuclease-induced Double-strand Break," The Journal of Gene Medicine, vol. 8, No. 5, pp. 616-622 (May 2006).
Gremillon, L. et al., "New plant growth-modifying properties of the Agrobacterium T-6b oncogene revealed by the use of a dexamethasone-inducible promoter," Plant J., vol. 37, No. 2, pp. 218-228 (Jan. 2004).
Grindl, W. et al., "The protein splicing domain of the homing endonuclease PI-SceI is responsible for specific DNA binding," Nucleic Acids Research, vol. 26, No. 8, pp. 1857-1862 (Apr. 15, 1998).

(56) References Cited

OTHER PUBLICATIONS

Guhan, N. and Muniyappa, K., "Structural and functional characteristics of homing endonucleases," Critical Reviews in Biochemistry and Molecular Biology, vol. 38, No. 3, pp. 199-248 (No Month Listed 2003).
Harris, J. L. and Craik, C. S., Engineering enzyme specificity. Curr. Opin. Chem. Biol., vol. 2, No. 1, pp. 127-132 (Feb. 1998).
Heath, P. J. et al. "The Structure of I-CreI, A Group I Intron-encoded Homing Endonuclease," Nature Structural Biology, vol. 4, No. 6., pp. 468-476 (Jun. 1997).
Hu, D. et al. "Probing the Structure of the PI-SceI-DNA Complex by Affinity Cleavage and Affinity Photcross-linking." The Journal of Biological Chemistry, vol. 275, No. 4, pp. 2705-2712 (Jan. 28, 2000).
Ichiyanagi, K. et al., "Crystal structure of an archaeal intein-encoded homing endonuclease PI-PfuI," J. Mol. Biol., vol. 300, No. 4, pp. 889-901 (Jul. 21, 2000).
International Search Report and Written Opinion for International Application No. PCT/US09/50566 mailed Oct. 20, 2009 (13 pages).
International Search Report for International Application No. PCT/US2006/040919 mailed Aug. 29, 2007 (9 pages).
Jurica, M. S. et al., "DNA recognition and cleavage by the LAGLIDADG homing endonuclease I-CreI," Molecular Cell, vol. 2, No. 4, pp. 469-476 (Oct. 1998).
Jurica, M.S. et al. "Homing Endonucleases: Structure, Function and Evolution," CMLS: Cellular and Molecular Life Sciences, vol. 55, No. 10, pp. 1304-1326 (Aug. 15, 1999).
Lloyd, A. et al., "Targeted mutagenesis using zinc-finger nucleases in Arabidopsis," PNAS, vol. 102, No. 6, pp. 2232-2237 (Feb. 8, 2005).
Looger, L. et al., "Computational Design of Receptor and Sensor Proteins with Novel Functions," Nature, vol. 423, No. 6936, pp. 185-190 (May 8, 2003).
Lorence, A. and Verpoorte, R., "Gene transfer and expression in plants," Methods Mol. Biol., vol. 267, pp. 329-350 (No Month Listed 2004).
Lucas, P. et al., "Rapid evolution of the DNA-binding site in LAGLIDADG homing endonucleases," Nucleic Acids Research, vol. 29, No. 4, pp. 960-969 (Feb. 15, 2001).
Maggert, K. A. and Golic, K. G., "Highly efficient sex chromosome interchanges produced by I-CreI expression in *Drosophila*," Genetics, vol. 171, No. 3, pp. 1103-1114 (Nov. 2005).
Mani, M. et al., "Binding of two zinc finger nuclease monomers to two specific sites is required for effective double-strand DNA cleavage," Biochemical and Biophysical Research Communications, vol. 334, No. 4, pp. 1191-1197 (Sep. 9, 2005).
Mani, M. et al., "Design, engineering, and characterization of zinc finger nucleases," Biochemical and Biophysical Research Communications, vol. 335, No. 2, pp. 447-457 (Sep. 23, 2005).
Matsumura, H. et al., "Crystal structure of intein homing endonuclease II encoded in DNA polymerase gene from hyperthermophilic archaeon Thermococcus kodakaraensis strain KOD1," Proteins, vol. 63, No. 3, pp. 711-715 (May 15, 2006).
McDaniel, R. and Weiss, R., "Advances in synthetic biology: on the path from prototypes to applications," Current Opinion in Biotechnology, vol. 16, No. 4, pp. 476-483 (Aug. 2005).
Monnat, R. J. Jr. et al., "Generation of highly site-specific DNA double-strand breaks in human cells by the homing endonucleases I-Ppol and I CreI," Biochemical and Biophysical Research Communications, vol. 255, No. 1, pp. 88-93 (Feb. 5, 1999).
Moure, C. M. et al., "Crystal structure of the intein homing endonuclease PI-SceI bound to its recognition sequence," Nature Structural Biology, vol. 9, No. 10, pp. 764-770 (Oct. 2002).
Moure, C. M. et al., "The crystal structure of the gene targeting homing endonuclease I-SceI reveals the origins of its target site specificity," J. Mol. Biol., vol. 334, No. 4, pp. 685-695 (Dec. 5, 2003).

Omirullen, S. et al., "Activity of a chimeric promoter with the doubled CaMV 35S enhancer element in protoplast-derived cells and transgenic plants in maize," Plant Mol. Biol., vol. 21, No. 3, pp. 415-428 (Feb. 1993).
Pabo, C. O. and Sauer, R. T., "Transcription factors: structural families and principles of DNA recognition," Annu. Rev. Biochem., vol. 61, pp. 1053-1095 (No Month Listed 1992).
Pace, C. Nick et al., "Protein Stability," Encyclopedia of Life Sciences, John Wiley & Sons Ltd., pp. 1-4 (No Month Listed 2001).
Poland, B. W. et al., "Structural Insights into the Protein Splicing Mechanism of PI-SceI," The Journal of Biological Chemistry, vol. 275, No. 22, pp. 16408-16413 (Jun. 2, 2000).
Porteus, M. H. and Carroll, D., "Gene targeting using zinc finger nucleases," Nature Biotechnology, vol. 23, No. 8, pp. 967-973 (Aug. 2005).
Porteus, Matthew H., "Mammalian gene targeting with designed zinc finger nucleases," Molecular Therapy, vol. 13, No. 2, pp. 438-446 (Feb. 2006).
Prieto, J. et al., "The C-terminal loop of the homing endonuclease I-CreI is essential for site recognition, DNA binding and cleavage," Nucleic Acids Research, vol. 35, No. 10, pp. 3262-3271 (No Month Listed 2007).
Puchta, H. et al., "Two different but related mechanisms are used in plants for the repair of genomic double-strand breaks by homologous recombination," Proc. Natl. Acad. Sci. USA, vol. 93, No. 10, pp. 5055-5060 (May 14, 1996).
Rong, Y. S. et al., "Targeted mutagenesis by homologous recombination in *D. melanogaster*," Genes & Dev., vol. 16, No. 12, pp. 1568-1581 (Jun. 15, 2002).
Rosen, L. E. et al., "Homing endonuclease I-CreI derivatives with novel DNA target specificities," Nucleic Acids Res., vol. 34, No. 17, pp. 4791-4800 (No Month Listed 2006).
Rouet, P. et al., "Introduction of double-strand breaks into the genome of mouse cells by expression of a rare-cutting endonuclease," Molecular and Cellular Biology, vol. 14, No. 12, pp. 8096-8106 (Dec. 1994).
Sali, A. and Blundell, T. L., "Comparative Protein Modelling by Satisfaction of Spatial Restraints," J. Mol. Biol., vol. 234, No. 3, pp. 779-815 (Dec. 5, 1993).
Salomon, S. and Puchta, H., "Capture of genomic and T-DNA sequence during double-strand break repair in somatic plant cells," EMBO J., vol. 17, No. 20, pp. 6086-6095 (Oct. 15, 1998).
Seligman, L. M. et al., "Genetic Analysis of the Chlamydomonas reinhardtii I-CreI mobile intron homing system in *Escherichia coli*," Genetics, vol. 147, No. 4, pp. 1653-1664 (Dec. 1997).
Seligman, L. M. et al., "Mutations altering the cleavage specificity of a homing endonuclease," Nucleic Acids Research, vol. 30, No. 17, pp. 3870-3879 (Sep. 1, 2002).
Shen, B. W. et al., "DNA binding and cleavage by the HNH homing endonuclease I-HmuI," J. Mol. Biol., vol. 342, No. 1, pp. 43-56 (Jul. 2004).
Silva, G. H. et al., "Analysis of the LAGLIDADG interface of the monomeric homing endonuclease I-DmoI," Nucleic Acids Research, vol. 32, No. 10, pp. 3156-3168 (Jun. 9, 2004).
Silva, G. H. et al., "Crystal structure of the thermostable archaeal intron-encoded endonuclease I-DmoI," J. Mol. Biol., vol. 286, No. 4, pp. 1123-1136 (Mar. 5, 1999).
Silva, G. H. et al., "From Monomeric to Homodimeric Endonucleases and Back: Engineering Novel Specificity of LAGLIDADG Enzymes," J. Mol. Biol., vol. 361, No. 4, pp. 744-754 (Aug. 25, 2006).
Singh, M. et al., "Isolation and characterization of a flowering plant male gametic cell-specific promoter," FEBS Lett., vol. 542, No. 1-2, pp. 47-52 (May 8, 2003).
Smith, J. et al., "A combinatorial approach to create artificial homing endonucleases cleaving chosen sequences," Nucleic Acids Research, vol. 34, No. 22, pp. 1-12 (No Month Listed 2006).
Smith, J. et al., "A detailed study of the substrate specificity of a chimeric restriction enzyme," Nucleic Acids Research, vol. 27, No. 2, pp. 674-681 (Jan. 15, 1999).

(56) References Cited

OTHER PUBLICATIONS

Smith, J. et al., "Requirements for double-strand cleavage by chimeric restriction enzymes with zinc finger DNA-recognition domains," Nucleic Acids Research, vol. 28, No. 17, pp. 3361-3369 (Sep. 1, 2000).

Spiegel, P. C. et al., "The structure of I-Ceul homing endonuclease: Evolving asymmetric DNA recognition from a symmetric protein scaffold," Structure, vol. 14, No. 5, pp. 869-880 (May 2006).

Stoddard, Barry L., "Homing endonuclease structure and function," Quarterly Reviews of Biophysics, vol. 38, No. 1, pp. 49-95, 47 pages (Feb. 2005).

Supplementary European Search Report for European Patent Application No. 09798667.3 mailed Sep. 7, 2011 (9 pages).

Sussman, D. et al., "Isolation and characterization of new homing endonuclease specificities at individual target site positions," J. Mol. Biol., vol. 342, No. 1, pp. 31-41 (Sep. 3, 2004).

Turmel, M. et al., "Evolutionary Conserved and Functionally Important Residues in the I-Ceul Homing Endonuclease," Nucleic Acid Research, vol. 25, No. 13, pp. 2610-2619 (Jul. 1, 1997).

Tzfira, T. and White, C., "Towards targeted mutagenesis and gene replacement in plants," Trends in Biotechnology, vol. 23, No. 12, pp. 567-569 (Dec. 2005).

Urnov, F. D. et al., "Designed transcription factors as structural, functional and therapeutic probes of chromatin in vivo," EMBO Reports, vol. 3, No. 7, pp. 610-615 (Jul. 2002).

Urnov, F. D. et al., "Highly efficient endogenous human gene correction using designed zinc-finger nucleases," Nature, vol. 435, No. 7042, pp. 646-651 (Jun. 2, 2005).

Van Roey, P. et al., "Catalytic domain structure and hypothesis for function of GIY-YIG intron endonuclease I-Tevl," Nat. Struct. Biol., vol. 9, No. 11, pp. 806-811 (Nov. 2002).

Wang, J. et al., "Purification, biochemical characterization and protein-DNA interactions of the I-Crel endonuclease produced in *Escherichia coli*," Nucleic Acids Research, vol. 25, No. 19, pp. 3767-3776 (Oct. 1, 1997).

Wende, W. et al., "Binding, bending and cleavage of DNA substrates by the homing endonuclease PI-Scel," Nucleic Acid Res., vol. 24, No. 21, pp. 4123-4132 (Nov. 1, 1996).

Wright, D. A. et al., "High-frequency homologous recombination in plants mediated by zinc-finger nucleases," Plant J., vol. 44, No. 4, pp. 693-705 (Nov. 2005).

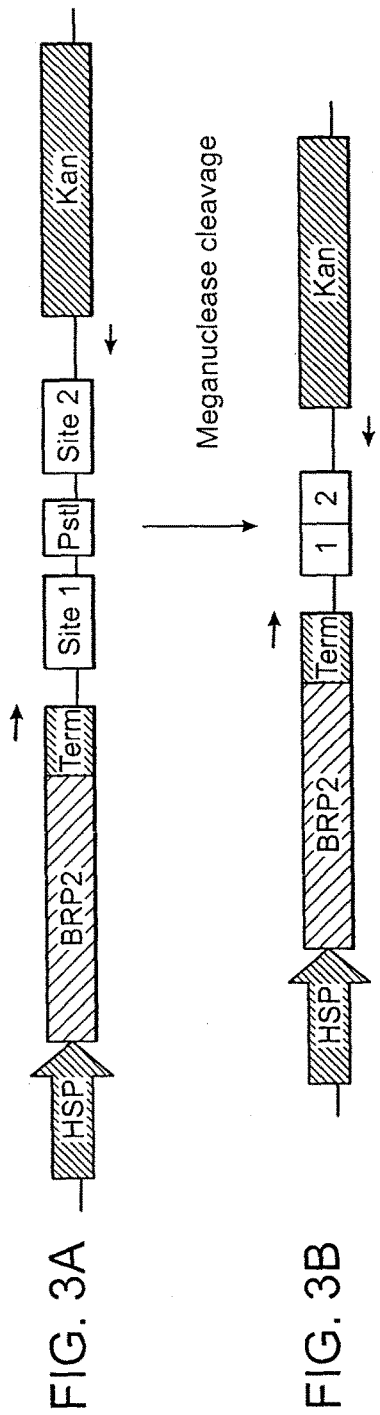
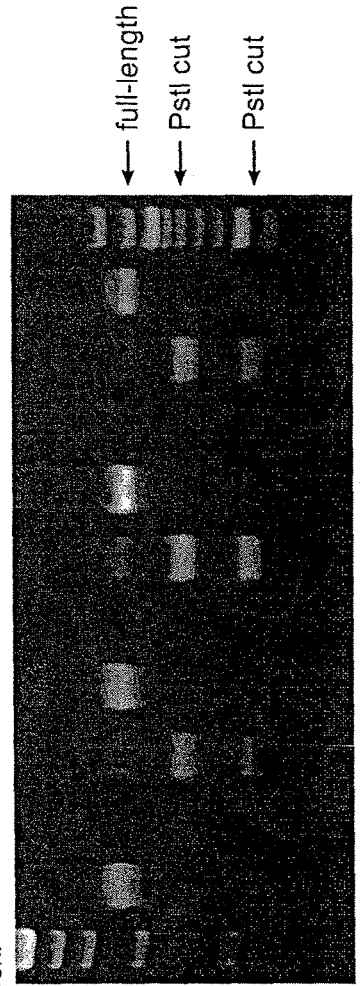
FIG. 3A
FIG. 3B
FIG. 3C   GTAC: CTCCGGGTCGTACGACCCGGAG
          TAGA: CTCCGGGTCTAGAGACCCGGAG
FIG. 3D

FIG. 4C  GTAC: TGCCTCCTCGTACGACCCGGAG
TAGA: TGCCTCCTCTAGAGACCCGGAG

SEQUENCE LISTING

<160> NUMBER OF SEQ ID NOS: 24

<210> SEQ ID NO 1
<211> LENGTH: 163
<212> TYPE: PRT
<213> ORGANISM: Chlamydomonas reinhardtii

<400> SEQUENCE: 1

```
Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
            20                  25                  30

Tyr Lys Phe Lys His Gln Leu Ser Leu Ala Phe Gln Val Thr Gln Lys
```

```
              35                  40                  45
Thr Gln Arg Arg Trp Phe Leu Asp Lys Leu Val Asp Glu Ile Gly Val
         50                  55                  60
Gly Tyr Val Arg Asp Arg Gly Ser Val Ser Asp Tyr Ile Leu Ser Glu
 65                  70                  75                  80
Ile Lys Pro Leu His Asn Phe Leu Thr Gln Leu Gln Pro Phe Leu Lys
                 85                  90                  95
Leu Lys Gln Lys Gln Ala Asn Leu Val Leu Lys Ile Ile Trp Arg Leu
            100                 105                 110
Pro Ser Ala Lys Glu Ser Pro Asp Lys Phe Leu Glu Val Cys Thr Trp
        115                 120                 125
Val Asp Gln Ile Ala Ala Leu Asn Asp Ser Lys Thr Arg Lys Thr Thr
    130                 135                 140
Ser Glu Thr Val Arg Ala Val Leu Asp Ser Leu Ser Glu Lys Lys Lys
145                 150                 155                 160
Ser Ser Pro

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gaaactgtct cacgacgttt tg                                          22

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
caaaacgtcg tgagacagtt tc                                          22

<210> SEQ ID NO 4
<211> LENGTH: 163
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Asn Thr Lys Tyr Asn Lys Glu Phe Leu Leu Tyr Leu Ala Gly Phe
  1               5                  10                  15
Val Asp Gly Asp Gly Ser Ile Ile Ala Gln Ile Asp Pro Arg Gln Asn
             20                  25                  30
Tyr Lys Phe Lys His Glu Leu Arg Leu Arg Phe Gln Val Thr Gln Lys
         35                  40                  45
Thr Gln Arg Arg Trp Phe Leu Asp Lys Leu Val Asp Glu Ile Gly Val
     50                  55                  60
Gly Tyr Val Arg Asp Arg Gly Ser Val Ser Asp Tyr Ile Leu Ser Glu
 65                  70                  75                  80
Ile Lys Pro Leu His Asn Phe Leu Thr Gln Leu Gln Pro Phe Leu Lys
                 85                  90                  95
```

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Ser Glu Lys Lys Lys
145                 150                 155                 160

Ser Ser Pro

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aacggtgtcg tgagacaccg tt                                              22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
aacggtgtct cacgacaccg tt                                              22

<210> SEQ ID NO 7
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7 aacggtgtc                                                              9

<210> SEQ ID NO 8
<211> LENGTH: 173
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Gly Pro Lys Lys Arg Lys Val Ile Met Asn Thr Lys Tyr Asn
1               5                   10                  15

Lys Glu Phe Leu Leu Tyr Leu Ala Gly Phe Val Asp Gly Asp Gly Ser
                20                  25                  30

Ile Ile Ala Ser Ile Arg Pro Arg Gln Ser Cys Lys Phe Lys His Glu
            35                  40                  45

Leu Glu Leu Arg Phe Gln Val Thr Gln Lys Thr Gln Arg Arg Trp Phe
        50                  55                  60

Leu Asp Lys Leu Val Asp Glu Ile Gly Val Gly Tyr Val Arg Asp Arg
65                  70                  75                  80

```
Gly Ser Val Ser Asp Tyr Arg Leu Ser Gln Ile Lys Pro Leu His Asn
                85                  90                  95

Phe Leu Thr Gln Leu Gln Pro Phe Leu Lys Leu Lys Gln Lys Gln Ala
            100                 105                 110

Asn Leu Val Leu Lys Ile Ile Glu Gln Leu Pro Ser Ala Lys Glu Ser
        115                 120                 125

Pro Asp Lys Phe Leu Glu Val Cys Thr Trp Val Asp Gln Ile Ala Ala
    130                 135                 140

Leu Asn Asp Ser Lys Thr Arg Lys Thr Thr Ser Glu Thr Val Arg Ala
145                 150                 155                 160

Val Leu Asp Ser Leu Ser Glu Lys Lys Lys Ser Ser Pro
            165                 170

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ctccgggtcg tacgacccgg ag                                              22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ctccgggtcg tacgacccgg ag                                              22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ctccgggtct agagacccgg ag                                              22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ctccgggtct ctagacccgg ag                                              22

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 13

Met Ala Pro Lys Lys Arg Lys Val
1               5

<210> SEQ ID NO 14
<211> LENGTH: 522
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
atgggcccga agaagaagcg caaggtcatc atgaacacca agtacaacaa ggagttcctg      60
ctctacctgg cgggcttcgt ggacggggac ggctccatca tcgcctccat ccgcccgcgt     120
cagtcctgca agttcaagca tgagctggaa ctccggttcc aggtcacgca agagacacag     180
cgccgttggt tcctcgacaa gctggtggac gagatcgggg tgggctacgt gcgcgaccgc     240
ggcagcgtct ccgactaccg cctgagccag atcaagcctc tgcacaactt cctgacccag     300
ctccagccct tcctgaagct caagcagaag caggccaacc tcgtgctgaa gatcatcgag     360
cagctgccct ccgccaagga atccccggac aagttcctgg aggtgtgcac ctgggtggac     420
cagatcgccg ctctgaacga ctccaagacc cgcaagacca cttccgagac cgtccgcgcc     480
gtgctggaca gtctctccga agaagaag tcgtcccct ag                          522
```

<210> SEQ ID NO 15
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Gly Pro Lys Lys Arg Lys Val Ile Met Asn Thr Lys Tyr Asn
1               5                   10                  15

Lys Glu Phe Leu Leu Tyr Leu Ala Gly Phe Val Asp Gly Asp Gly Ser
            20                  25                  30

Ile Lys Ala Gln Ile Arg Pro Arg Gln Ser Arg Lys Phe Lys His Glu
        35                  40                  45

Leu Glu Leu Thr Phe Gln Val Thr Gln Lys Thr Gln Arg Arg Trp Phe
    50                  55                  60

Leu Asp Lys Leu Val Asp Glu Ile Gly Val Gly Lys Val Tyr Asp Arg
65                  70                  75                  80

Gly Ser Val Ser Asp Tyr Glu Leu Ser Gln Ile Lys Pro Leu His Asn
                85                  90                  95

Phe Leu Thr Gln Leu Gln Pro Phe Leu Lys Leu Lys Gln Lys Gln Ala
            100                 105                 110

Asn Leu Val Leu Lys Ile Ile Glu Gln Leu Pro Ser Ala Lys Glu Ser
        115                 120                 125

Pro Asp Lys Phe Leu Glu Val Cys Thr Trp Val Asp Gln Ile Ala Ala
    130                 135                 140

Leu Asn Asp Ser Lys Thr Arg Lys Thr Thr Ser Glu Thr Val Arg Ala
145                 150                 155                 160

Val Leu Asp Ser Leu Pro Gly Ser Val Gly Gly Leu Ser Pro Ser Gln
                165                 170                 175

```
Ala Ser Ser Ala Ala Ser Ser Ala Ser Ser Pro Gly Ser Gly Ile
            180                 185                 190

Ser Glu Ala Leu Arg Ala Gly Ala Thr Lys Ser Lys Glu Phe Leu Leu
        195                 200                 205

Tyr Leu Ala Gly Phe Val Asp Gly Asp Gly Ser Ile Ile Ala Ser Ile
    210                 215                 220

Arg Pro Arg Gln Ser Cys Lys Phe Lys His Glu Leu Glu Leu Arg Phe
225                 230                 235                 240

Gln Val Thr Gln Lys Thr Gln Arg Arg Trp Phe Leu Asp Lys Leu Val
                245                 250                 255

Asp Glu Ile Gly Val Gly Tyr Val Arg Asp Arg Gly Ser Val Ser Asp
            260                 265                 270

Tyr Arg Leu Ser Gln Ile Lys Pro Leu His Asn Phe Leu Thr Gln Leu
        275                 280                 285

Gln Pro Phe Leu Lys Leu Lys Gln Lys Gln Ala Asn Leu Val Leu Lys
    290                 295                 300

Ile Ile Glu Gln Leu Pro Ser Ala Lys Glu Ser Pro Asp Lys Phe Leu
305                 310                 315                 320

Glu Val Cys Thr Trp Val Asp Gln Ile Ala Ala Leu Asn Asp Ser Lys
                325                 330                 335

Thr Arg Lys Thr Thr Ser Glu Thr Val Arg Ala Val Leu Asp Ser Leu
            340                 345                 350

Ser Glu Lys Lys Lys Ser Ser Pro
        355                 360
```

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tgcctcctcg tacgacccgg ag                                              22

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ctccgggtcg tacgaggagg ca                                              22

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tgcctcctct agagacccgg ag                                              22

<210> SEQ ID NO 19
<211> LENGTH: 22
<212> TYPE: DNA

<213> ORGANISM: Artificial Sequence
<220> FEATURE:
<223> OTHER INFORMATION: Description of Artificial Sequence: Synthetic oligonucleotide

<400> SEQUENCE: 19

```
ctccgggtct ctagaggagg ca                                              22
```

<210> SEQ ID NO 20
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 20

```
Pro Gly Ser Val Gly Gly Leu Ser Pro Ser Gln Ala Ser Ser Ala Ala
1               5                   10                  15

Ser Ser Ala Ser Ser Ser Pro Gly Ser Gly Ile Ser Glu Ala Leu Arg
            20                  25                  30

Ala Gly Ala Thr Lys Ser
        35
```

<210> SEQ ID NO 21
<211> LENGTH: 1083
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21

```
atgggcccga agaagaagcg caaggtcatc atgaacacca agtacaacaa ggagttcctg     60
ctctacctgg ccggcttcgt ggacggcgac ggctccatca aggcgcagat ccgtccgcgg    120
cagagccgga agttcaagca cgagctcgag ctgaccttcc aggtgaccca gaagacgcag    180
aggcgctggt cctcgacaa gctggtggac gagatcgggg tgggcaaggt ctacgaccgc    240
gggtcggtgt ccgactacga gctctcccag atcaagcccc tgcacaactt cctcacccag    300
ctccagccgt tcctgaagct caagcagaag caggccaacc tcgtgctgaa gatcatcgag    360
cagctgccct ccgccaagga atccccggac aagttcctgg aggtgtgcac gtgggtggac    420
cagatcgcgg ccctcaacga cagcaagacc cgcaagacga cctcggagac ggtgcgggcg    480
gtcctggact ccctcccagg atccgtggga ggtctatcgc catctcaggc atccagcgcc    540
gcatcctcgg cttcctcaag cccgggttca gggatctccg aagcactcag agctggagca    600
actaagtcca aggaattcct gctctacctg gcgggcttcg tggacgggga cggctccatc    660
atcgcctcca tccgcccgcg tcagtcctgc aagttcaagc atgagctgga actccggttc    720
caggtcacgc agaagacaca cgccgttgg ttcctcgaca agctggtgga cgagatcggg    780
gtgggctacg tgcgcgaccg cggcagcgtc tccgactacc gctgagcca gatcaagcct    840 ctgcacaact tcctgaccca gctccagccc ttcctgaagc tcaagcagaa gcaggccaac    900
ctcgtgctga gatcatcga gcagctgccc tccgccaagg aatccccgga caagttcctg    960
gaggtgtgca cctgggtgga ccagatcgcc gctctgaacg actccaagac ccgcaagacc   1020
acttccgaga ccgtccgcgc cgtgctggac agtctctccg agaagaagaa gtcgtccccc   1080
tag                                                                1083
```

```
<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(13)
<223> OTHER INFORMATION: a, c, t, g, unknown or other

<400> SEQUENCE: 22
aacggtgtcn nnngacaccg tt                                              22

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(13)
<223> OTHER INFORMATION: a, c, t, g, unknown or other

<400> SEQUENCE: 23
aacggtgtcn nnngacaccg tt                                              22

<210> SEQ ID NO 24
<211> LENGTH: 9
<212> TYPE: PRT
<213> ORGANISM: Unknown
<220> FEATURE:
<223> OTHER INFORMATION: Description of Unknown: "LAGLIDADG" family
      motif peptide

<400> SEQUENCE: 24

Leu Ala Gly Leu Ile Asp Ala Asp Gly
1               5
```

US 9,683,257 B2

RECOGNITION SEQUENCES FOR I-CREI-DERIVED MEGANUCLEASES AND USES THEREOF

REFERENCE TO RELATED APPLICATIONS

This application is a Continuation of U.S. patent application Ser. No. 13/006,625, filed on Jan. 14, 2011, which is a Continuation of International Application PCT/US2009/50566 filed on Jul. 14, 2009, which claims the benefit of U.S. Provisional Application No. 61/080,453, filed Jul. 14, 2008, the entire disclosures of which are incorporated herein by reference.

SEQUENCE LISTING

The instant application contains a Sequence Listing which has been submitted electronically in ASCII format and is hereby incorporated by reference in its entirety. Said ASCII copy, created on Jun. 26, 2014, is named 2000706.00131US2_SL.txt and is 15,334 bytes in size.

FIELD OF THE INVENTION

The invention relates to the field of molecular biology and recombinant nucleic acid technology. In particular, the invention relates to DNA sequences that can be recognized and cleaved by a non-naturally-occurring, rationally-designed, I-CreI-derived homing endonuclease and methods of using same. The invention also relates to methods of producing recombinant nucleic acids, cells, and organisms using such meganucleases which cleave such DNA sites. The invention further relates to methods of conducting a custom-designed, I-CreI-derived meganuclease business.

BACKGROUND OF THE INVENTION

Genome engineering requires the ability to insert, delete, substitute and otherwise manipulate specific genetic sequences within a genome, and has numerous therapeutic and biotechnological applications. The development of effective means for genome modification remains a major goal in gene therapy, agrotechnology, and synthetic biology (Porteus et al. (2005), *Nat. Biotechnol.* 23: 967-73; Tzfira et al. (2005), *Trends Biotechnol.* 23: 567-9; McDaniel et al. (2005), *Curr. Opin. Biotechnol.* 16: 476-83). A common method for inserting or modifying a DNA sequence involves introducing a transgenic DNA sequence flanked by sequences homologous to the genomic target and selecting or screening for a successful homologous recombination event. Recombination with the transgenic DNA occurs rarely, but can be stimulated by a double-stranded break in the genomic DNA at the target site. Numerous methods have been employed to create DNA double-stranded breaks, including irradiation and chemical treatments. Although these methods efficiently stimulate recombination, the double-stranded breaks are randomly dispersed in the genome, which can be highly mutagenic and toxic. At present, the inability to target gene modifications to unique sites within a chromosomal background is a major impediment to successful genome engineering.

One approach to achieving this goal is stimulating homologous recombination at a double-stranded break in a target locus using a nuclease with specificity for a sequence that is sufficiently large to be present at only a single site within the genome (see, e.g., Porteus et al. (2005), *Nat. Biotechnol.* 23: 967-73). The effectiveness of this strategy has been demonstrated in a variety of organisms using chimeric fusions between an engineered zinc finger DNA-binding domain and the non-specific nuclease domain of the FokI restriction enzyme (Porteus (2006), *Mol Ther* 13: 438-46; Wright et al. (2005), *Plant J.* 44: 693-705; Urnov et al. (2005), *Nature* 435: 646-51). Although these artificial zinc finger nucleases stimulate site-specific recombination, they retain residual non-specific cleavage activity resulting from under-regulation of the nuclease domain and frequently cleave at unintended sites (Smith et al. (2000), *Nucleic Acids Res.* 28: 3361-9). Such unintended cleavage can cause mutations and toxicity in the treated organism (Porteus et al. (2005), *Nat. Biotechnol.* 23: 967-73).

A group of naturally-occurring nucleases which recognize 15-40 base-pair cleavage sites commonly found in the genomes of plants and fungi may provide a less toxic genome engineering alternative. Such "meganucleases" or "homing endonucleases" are frequently associated with parasitic DNA elements, such as group 1 self-splicing introns and inteins. They naturally promote homologous recombination or gene insertion at specific locations in the host genome by producing a double-stranded break in the chromosome, which recruits the cellular DNA-repair machinery (Stoddard (2006), *Q. Rev. Biophys.* 38: 49-95). Meganucleases are commonly grouped into four families: the LAGLIDADG (SEQ ID NO: 24) family, the GIY-YIG family, the His-Cys box family and the HNH family. These families are characterized by structural motifs, which affect catalytic activity and recognition sequence. For instance, members of the LAGLIDADG (SEQ ID NO: 24) family are characterized by having either one or two copies of the conserved LAGLIDADG (SEQ ID. NO: 24) motif (see Chevalier et al. (2001), *Nucleic Acids Res.* 29(18): 3757-3774). The LAGLIDADG (SEQ ID NO: 24) meganucleases with a single copy of the LAGLIDADG (SEQ ID NO: 24) motif form homodimers, whereas members with two copies of the LAGLIDADG (SEQ ID NO: 24) motif are found as monomers.

Natural meganucleases, primarily from the LAGLIDADG (SEQ ID NO: 24) family, have been used to effectively promote site-specific genome modification in plants, yeast, *Drosophila*, mammalian cells and mice, but this approach has been limited to the modification of either homologous genes that conserve the meganuclease recognition sequence (Monnat et al. (1999), *Biochem. Biophys. Res. Commun.* 255: 88-93) or to pre-engineered genomes into which a recognition sequence has been introduced (Rouet et al. (1994), *Mol. Cell. Biol.* 14: 8096-106; Chilton et al. (2003), *Plant Physiol.* 133: 956-65; Puchta et al. (1996), *Proc. Natl. Acad. Sci. USA* 93: 5055-60; Rong et al. (2002), *Genes Dev.* 16: 1568-81; Gouble et al. (2006), *J. Gene Med.* 8(5):616-622).

Systematic implementation of nuclease-stimulated gene modification requires the use of engineered enzymes with customized specificities to target DNA breaks to existing sites in a genome and, therefore, there has been great interest in adapting meganucleases to promote gene modifications at medically or biotechnologically relevant sites (Porteus et al. (2005), *Nat. Biotechnol.* 23: 967-73; Sussman et al. (2004), *J. Mol. Biol.* 342: 31-41; Epinat et al. (2003), *Nucleic Acids Res.* 31: 2952-62).

I-CreI (SEQ ID NO: 1) is a member of the LAGLIDADG (SEQ ID NO: 24) family which recognizes and cleaves a 22 base pair recognition sequence in the chloroplast chromosome, and which presents an attractive target for meganuclease redesign. Genetic selection techniques have been used to modify the wild-type I-CreI recognition site preference (Sussman et al. (2004), *J. Mol. Biol.* 342: 31-41; Chames et al. (2005), *Nucleic Acids Res.* 33: e178; Seligman et al. (2002), *Nucleic Acids Res.* 30: 3870-9, Arnould et al. (2006), *J. Mol. Biol.* 355: 443-58). More recently, a method of rationally-designing mono-LAGLIDADG (SEQ ID NO: 24) meganucleases was described which is capable of comprehensively redesigning I-CreI and other such meganucleases to target widely-divergent DNA sites, including sites in mammalian, yeast, plant, bacterial, and viral genomes (WO 2007/047859).

The DNA sequences recognized by I-CreI are 22 base pairs in length. One example of a naturally-occurring I-CreI recognition site is provided in SEQ ID NO: 2 and SEQ ID NO: 3, but the enzyme will bind to a variety of related sequences with varying affinity. The enzyme binds DNA as a homodimer in which each monomer makes direct contacts with a nine base pair "half-site" and the two half-sites are separated by four base pairs that are not directly contacted by the enzyme (FIG. 1a). Like all LAGLIDADG (SEQ ID NO: 24) family meganucleases, I-CreI produces a staggered double-strand break at the center of its recognition sequences which results in the production of a four base pair 3'-overhang (FIG. 1a). The present invention concerns the central four base pairs in the I-CreI recognition sequences (i.e. the four base pairs that become the 3' overhang following I-CreI cleavage, or "center sequence", FIG. 1b). In the case of the native I-CreI recognition sequence in the *Chlamydomonas reinhardtii* 23S rRNA gene, this four base pair sequence is 5'-GTGA-3'. In the interest of producing genetically-engineered meganucleases which recognize DNA sequences that deviate from the wild-type I-CreI recognition sequences, it is desirable to know the extent to which the four base pair center sequence can deviate from the wild-type sequences. A number of published studies concerning I-CreI or its derivatives evaluated the enzyme, either wild-type or genetically-engineered, using DNA substrates that employed either the native 5'-GTGA-3' central sequence or the palindromic sequence 5'-GTAC-3'. Recently, Arnould et. al. (Arnould et al. (2007), *J. Mol. Biol.* 371: 49-65) reported that a set of genetically-engineered meganucleases derived from I-CreI cleaved DNA substrates with varying efficiencies depending on whether the substrate sequences were centered around 5'-GTAC-3', 5'-TTGA-3', 5'-GAAA-3', or 5'-ACAC-3' (cleavage efficiency: GTAC>ACAC>> TTGA≈GAAA).

SUMMARY OF THE INVENTION

The present invention is based, in part, upon the identification and characterization of a subset of DNA recognition sequences that can act as efficient substrates for cleavage by the rationally-designed, I-CreI-derived meganucleases (hereinafter, "I-CreI-derived meganucleases").

In one aspect, the invention provides methods of identifying sets of 22 base pair DNA sequences which can be cleaved by I-CreI-derived meganucleases and which have, at their center, one of a limited set of four base pair DNA center sequences that contribute to more efficient cleavage by the I-CreI-derived meganucleases. The invention also provides methods that use such DNA sequences to produce recombinant nucleic acids, cells and organisms by utilizing the recognition sequences as substrates for I-CreI-derived meganucleases, and products incorporating such DNA sequences.

Thus, in one aspect, the invention provides a method for cleaving a double-stranded DNA comprising: (a) identifying in the DNA at least one recognition site for a rationally-designed I CreI-derived meganuclease with altered specificity relative to I-CreI, wherein the recognition site is not cleaved by a naturally-occurring I-CreI, wherein the recognition site has a four base pair central sequence selected from the group consisting of TTGT, TTAT, TCTT, TCGT, TCAT, GTTT, GTCT, GGAT, GAGT, GAAT, ATGT, TTTC, TTCC, TGAC, TAAC, GTTC, ATAT, TCGA, TTAA, GGGC, ACGC, CCGC, CTGC, ACAA, ATAA, AAGA, ACGA, ATGA, AAAC, AGAC, ATCC, ACTC, ATTC, ACAT, GAAA, GGAA, GTCA, GTTA, GAAC, ATAT, TCGA, TTAA, GCCC, GCGT, GCGG and GCAG; (b) providing the rationally-designed meganuclease; and (c) contacting the DNA with the rationally-designed meganuclease; whereby the rationally-designed meganuclease cleaves the DNA.

In another aspect, the invention provides a method for cleaving a double-stranded DNA comprising: (a) introducing into the DNA a recognition site for a rationally-designed I CreI derived meganuclease with altered specificity relative to I-CreI, wherein the recognition site is not cleaved by a naturally-occurring I-CreI, wherein the recognition site has a four base pair central sequence selected from the group consisting of TTGT, TTAT, TCTT, TCGT, TCAT, GTTT, GTCT, GGAT, GAGT, GAAT, ATGT, TTTC, TTCC, TGAC, TAAC, GTTC, ATAT, TCGA, TTAA, GGGC, ACGC, CCGC, CTGC, ACAA, ATAA, AAGA, ACGA, ATGA, AAAC, AGAC, ATCC, ACTC, ATTC, ACAT, GAAA, GGAA, GTCA, GTTA, GAAC, ATAT, TCGA, TTAA, GCCC, GCGT, GCGG and GCAG; and (b) providing the rationally-designed meganuclease; and (c) contacting the DNA with the rationally-designed meganuclease; whereby the rationally-designed meganuclease cleaves the DNA.

In some embodiments, the four base pair DNA sequence is selected from the group consisting of GTGT, GTAT, TTAG, GTAG, TTAC, TCTC, TCAC, GTCC, GTAC, TCGC, AAGC, GAGC, GCGC, GTGC, TAGC, TTGC, ATGC, ACAC, ATAC, CTAA, CTAC, GTAA, GAGA, GTGA, GGAC, GTAC, GCGA, GCTT, GCTC, GCGC, GCAC, GCTA, GCAA and GCAT.

In some embodiments, the DNA cleavage is in vitro. In other embodiments, the DNA cleavage is in vivo.

In some embodiments, the DNA is selected from the group consisting of a PCR product; an artificial chromosome; genomic DNA isolated from bacteria, fungi, plants, or animal cells; and viral DNA.

In some embodiments, the DNA is present in a cell selected from the group consisting of a bacterial, fungal, plant and animal cell.

In some embodiments, the DNA is present in a nucleic acid selected from the group consisting of a plasmid, a prophage and a chromosome.

In certain embodiments, the method further comprises rationally-designing the I CreI derived meganuclease to recognize the recognition site.

In some embodiments, the method further comprises producing the rationally-designed I-CreI-derived meganuclease.

In another aspect, the invention provides a cell transformed with a nucleic acid comprising, in order: a) a first 9 base pair DNA sequence which can be bound by an I CreI derived meganuclease monomer or by a first domain from a single-chain I CreI derived meganuclease; b) a four base pair DNA sequence selected from the group consisting of GTGT, GTAT, TTAG, GTAG, TTAC, TCTC, TCAC, GTCC, GTAC, TCGC, AAGC, GAGC, GCGC, GTGC, TAGC, TTGC, ATGC, ACAC, ATAC, CTAA, CTAC, GTAA, GAGA, GTGA, GGAC, GTAC, GCGA, GCTT, GCTC, GCGC, GCAC, GCTA, GCAA and GCAT; and c) a second 9 base pair DNA sequence which can be bound by an I CreI derived meganuclease monomer or by a second domain from the single-chain I CreI derived meganuclease, wherein the second 9 base pair DNA sequence is in the reverse orientation relative to the first.

In yet another aspect, the invention provides a cell containing an exogenous nucleic acid sequence integrated into its genome, comprising, in order: a) a first exogenous 9 base pair DNA sequence which can be bound by an I CreI derived meganuclease monomer or by a first domain from a single-chain I CreI derived meganuclease; b) an exogenous four base pair DNA sequence selected from the group consisting of GTGT, GTAT, TTAG, GTAG, TTAC, TCTC, TCAC, GTCC, GTAC, TCGC, AAGC, GAGC, GCGC, GTGC, TAGC, TTGC, ATGC, ACAC, ATAC, CTAA, CTAC, GTAA, GAGA, GTGA, GGAC, GTAC, GCGA, GCTT, GCTC, GCGC, GCAC, GCTA, GCAA and GCAT; and a) a second exogenous 9 base pair DNA sequence which can be bound by an I CreI derived meganuclease monomer or by a second domain from the single-chain I CreI derived meganuclease, wherein the second 9 base pair DNA sequence is in the reverse orientation relative to the first.

In some embodiments, the nucleic acid is a plasmid, an artificial chromosome, or a viral nucleic acid.

In some embodiments, the cell is a non-human animal cell, a plant cell, a bacterial cell, or a fungal cell.

In some embodiments, the four base pair DNA sequence is TTGT, TTAT, TCTT, TCGT, TCAT, GTTT, GTCT, GGAT, GAGT, GAAT, ATGT, TTTC, TTCC, TGAC, TAAC, GTTC, ATAT, TCGA, TTAA, GGGC, ACGC, CCGC, CTGC, ACAA, ATAA, AAGA, ACGA, ATGA, AAAC, AGAC, ATCC, ACTC, ATTC, ACAT, GAAA, GGAA, GTCA, GTTA, GAAC, ATAT, TCGA, TTAA, GCCC, GCGT, GCGG or GCAG.

In some embodiments, the four base pair DNA sequence is GTGT, GTAT, TTAG, GTAG, TTAC, TCTC, TCAC, GTCC, GTAC, TCGC, AAGC, GAGC, GCGC, GTGC, TAGC, TTGC, ATGC, ACAC, ATAC, CTAA, CTAC, GTAA, GAGA, GTGA, GGAC, GTAC, GCGA, GCTT, GCTC, GCGC, GCAC, GCTA, GCAA or GCAT.

In yet another aspect, the invention provides a method of conducting a custom-designed, I-CreI-derived meganuclease business comprising: (a) receiving a DNA sequence into which a double-strand break is to be introduced by a rationally-designed I CreI-derived meganuclease; (b) identifying in the DNA sequence at least one recognition site for a rationally-designed I CreI-derived meganuclease with altered specificity relative to I-CreI, wherein the recognition site is not cleaved by a naturally-occurring I-CreI, wherein the recognition site has a four base pair central sequence selected from the group consisting of TTGT, TTAT, TCTT, TCGT, TCAT, GTTT, GTCT, GGAT, GAGT, GAAT, ATGT, TTTC, TTCC, TGAC, TAAC, GTTC, ATAT, TCGA, TTAA, GGGC, ACGC, CCGC, CTGC, ACAA, ATAA, AAGA, ACGA, ATGA, AAAC, AGAC, ATCC, ACTC, ATTC, ACAT, GAAA, GGAA, GTCA, GTTA, GAAC, ATAT, TCGA, TTAA, GCCC, GCGT, GCGG and GCAG; and (c) providing the rationally-designed meganuclease.

In some embodiments, the method further comprises rationally-designing the I CreI derived meganuclease to recognize the recognition site.

In some embodiments, the method further comprises producing the rationally-designed meganuclease.

In some embodiments, the rationally-designed meganuclease is provided to the same party from which the DNA sequence has been received.

These and other aspects and embodiments of the invention will be apparent to one of ordinary skill in the art from the following detailed description of the invention, figures and appended claims.

BRIEF DESCRIPTION OF THE FIGURES

FIG. 3. (A) Schematic diagram of a T-DNA that was stably integrated into the *Arabidopsis thaliana* genome as described in Example 1. In this T-DNA construct, a codon-optimized gene encoding the genetically-engineered BRP2 meganuclease (BRP2) (SEQ ID NO: 8) is under the control of a Hsp70 promoter (HSP) and a NOS terminator (TERM). A pair of potential BRP2 recognition sequences (Site1, Site2) are housed adjacent to the terminator separated by 7 base pairs containing a PstI restriction enzyme site (PstI). A kanamycin resistance marker (Kan) is also housed on the T-DNA to allow selection for stable transformants. (B) The expected product following BRP2 meganuclease cleavage of Site1 and Site2 showing loss of the intervening 7 base pair fragment and PstI restriction site. Arrows show the location of PCR primers used to screen for cleavage of the T-DNA. (C) Sequences of the BRP2 recognition sequences housed on either the GTAC construct (SEQ ID NO: 9) (GTAC) or the TAGA construct (SEQ ID NO: 11) (TAGA) with center sequences underlined. (D) Example of electrophoresis data from a plant transformed with the GTAC construct. Genomic DNA was isolated from the leaves of *Arabidopsis* seedlings stably transformed with either the GTAC T-DNA construct before and after a 2 hour "heat-shock" to induce BRP2 expression. DNA samples were then added to PCR reactions using the primers shown in (B). PCR reactions were digested with PstI and visualized by gel electrophoresis. C: control lane lacking PstI. 44, 45, and 46: PCR samples from three representative plants showing nearly complete digestion by PstI in samples taken prior to heat shock (−lanes) and very little digestion by PstI in samples taken after heat-shock (+lanes). These results indicate that the BRP2 meganuclease was able to cleave the BRP2 recognition sequence which incorporated a GTAC center sequence in vivo.

DETAILED DESCRIPTION OF THE INVENTION

1.1 Introduction

Figures 1A, 1B:
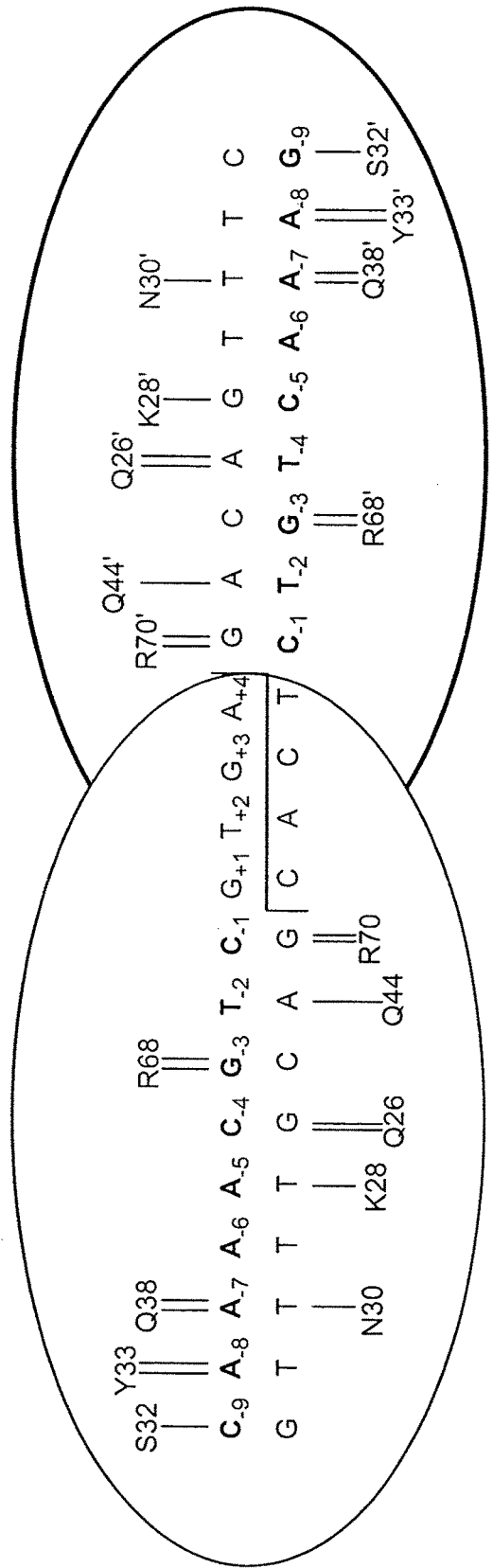
FIG. 1. (A) Schematic illustration of the interactions between the naturally-occurring I-CreI homodimer and a double-stranded recognition sequence, based upon crystallographic data. This schematic representation depicts one recognition sequence (SEQ ID NOS 3 and 2, respectively, in order of appearance), shown as unwound for illustration purposes only, bound by the homodimer, shown as two ovals. The bases of each DNA half-site are numbered −1 through −9, and the amino acid residues of I-CreI which form the recognition surface are indicated by one-letter amino acid designations and numbers indicating residue position. The four base pairs that comprise the center sequence are numbered +1 to +4. Solid black lines: hydrogen bonds to DNA bases. (B) One wild-type I-CreI recognition sequence (SEQ ID NOS 3 and 2, respectively, in order of appearance) showing the locations of the inverted half-sites and center sequence.

The present invention is based, in part, upon the identification and characterization of particular DNA sequences that are more efficiently cleaved by the rationally-designed, I-CreI-derived meganucleases. Specifically, the invention is based on the discovery that certain four-base pair DNA sequences, when incorporated as the central four-base pairs of a rationally-designed, I-CreI-derived meganuclease recognition sequence, can significantly impact cleavage by the corresponding meganuclease although the meganuclease does not, based upon analysis of crystal structures, appear to contact the central four base pairs. As there are four DNA bases (A, C, G, and T), there are $4^4$ or 256 possible DNA sequences that are four base pairs in length. All of these possible sequences were examined to determine the subsets of sequences that are more efficiently cleaved by I-CreI-derived meganucleases. The results of this analysis allow for more accurate prediction of whether or not a particular double-stranded DNA site 22 base pairs in length can be more efficiently cleaved by the I-CreI-derived meganuclease.

1.2 References and Definitions

The patent and scientific literature referred to herein establishes knowledge that is available to those of skill in the art. The issued U.S. patents, allowed applications, published foreign applications, and references, including GenBank database sequences, that are cited herein are hereby incorporated by reference to the same extent as if each was specifically and individually indicated to be incorporated by reference.

As used herein, the term "I-CreI-derived meganuclease" refers to a rationally-designed (i.e., genetically-engineered) meganuclease that is derived from I-CreI. The term genetically-engineered meganuclease, as used herein, refers to a recombinant variant of an I-CreI homing endonuclease that has been modified by one or more amino acid insertions, deletions or substitutions that affect one or more of DNA-binding specificity, DNA cleavage activity, DNA-binding affinity, and/or dimerization properties. Some genetically-engineered meganucleases are known in the art (see, e.g., Porteus et al. (2005), *Nat. Biotechnol.* 23: 967-73; Sussman et al. (2004), *J. Mol. Biol.* 342: 31-41; Epinat et al. (2003), *Nucleic Acids Res.* 31: 2952-62) and a general method for rationally-designing such variants is disclosed in WO 2007/047859. Additional methods for genetically-engineering such variants are disclosed in WO 04/067736, WO 07/060, 495, WO 06/097853, WO 07/049,095, WO 08/102,198, WO 08/010,093, WO 08/010,009, WO 07/093,918, WO 07/093, 836, WO 08/102,274, WO 08/059,317, WO 09/013,622, WO 09/019,614, WO 09/019,528, WO 08/152,523, WO 04/067753, WO 03/078619, WO 06/097784, WO 07/034, 262, WO 07/049,156, WO 07/057,781, WO 08/093,152, WO 08/102,199, WO 08/102,274, WO 08/149,176, WO 09/013,559, WO 09/013,622, and WO 09/019,528.

A meganuclease may bind to double-stranded DNA as a homodimer, as is the case for wild-type I-CreI, or it may bind to DNA as a heterodimer. A meganuclease may also be a "single-chain heterodimer" in which a pair of DNA-binding domains derived from I-CreI are joined into a single polypeptide using a peptide linker. The term "homing endonuclease" is synonymous with the term "meganuclease."

As used herein, the term "rationally-designed" means non-naturally occurring and/or genetically engineered. The rationally-designed meganucleases of the invention differ from wild-type or naturally-occurring meganucleases in their amino acid sequence or primary structure, and may also differ in their secondary, tertiary or quaternary structure. In addition, the rationally-designed meganucleases of the invention also differ from wild-type or naturally-occurring meganucleases in recognition sequence-specificity and/or activity.

As used herein, with respect to a protein, the term "recombinant" means having an altered amino acid sequence as a result of the application of genetic engineering techniques to nucleic acids which encode the protein, and cells or organisms which express the protein. With respect to a nucleic acid, the term "recombinant" means having an altered nucleic acid sequence as a result of the application of genetic engineering techniques. Genetic engineering techniques include, but are not limited to, PCR and DNA cloning technologies; transfection, transformation and other gene transfer technologies; homologous recombination; site-directed mutagenesis; and gene fusion. In accordance with this definition, a protein having an amino acid sequence identical to a naturally-occurring protein, but produced by cloning and expression in a heterologous host, is not considered recombinant.

As used herein, the term "genetically-modified" refers to a cell or organism in which, or in an ancestor of which, a genomic DNA sequence has been deliberately modified by recombinant technology. As used herein, the term "genetically-modified" encompasses the term "transgenic."

As used herein, the term "wild-type" refers to any naturally-occurring form of a meganuclease. The term "wild-type" is not intended to mean the most common allelic variant of the enzyme in nature but, rather, any allelic variant found in nature. Wild-type meganucleases are distinguished from recombinant or non-naturally-occurring meganucleases.

As used herein, the term "recognition sequence half-site" or simply "half site" means a 9 base pair DNA sequence which is recognized by a meganuclease monomer, in the case of a dimeric meganuclease, or by one domain of a single-chain meganuclease.

As used herein, the term "recognition sequence" refers to a pair of half-sites which is bound and cleaved by a meganuclease. A recognition sequence comprises a pair of inverted, 9 base pair half sites separated by four base-pairs. The recognition sequence is, therefore, 22 base-pairs in length. The base pairs of each half-site are designated −9 through −1, with the −9 position being most distal from the cleavage site and the −1 position being adjacent to the 4 base pair center sequence, the base pairs of which are designated +1 through +4. The strand of each half-site which is oriented 5' to 3' in the direction from −9 to −1 (i.e., towards the cleavage site), is designated the "sense" strand, and the opposite strand is designated the "antisense strand", although neither strand may encode protein. Thus, the "sense" strand of one half-site is the antisense (opposite) strand of the other half-site. See, for example, FIG. 1a.

As used herein, the term "center sequence" refers to the four base pairs separating half sites in the meganuclease recognition sequence. These bases are numbered +1 through +4 in FIG. 1a. The center sequence comprises the four bases that become the 3' single-strand overhangs following meganuclease cleavage. "Center sequence" can refer to the sequence of the sense strand or the antisense (opposite) strand.

As used herein, the term "specificity" refers to the ability of a meganuclease to recognize and cleave double-stranded DNA molecules only at a particular subset of all possible recognition sequences. The set of recognition sequences will share certain conserved positions or sequence motifs, but may be degenerate at one or more positions. A more specific meganuclease is capable of binding and cleaving a smaller subset of the possible recognition sequences, whereas a less specific meganuclease is capable of binding and cleaving a larger subset of the possible recognition sequences.

As used herein, the term "palindromic" refers to a recognition sequence consisting of inverted repeats of identical half-sites. In this case, however, the palindromic sequence need not be palindromic with respect to the center sequence, which is not contacted by the enzyme. In the case of dimeric meganucleases, palindromic DNA sequences are recognized by homodimers in which the two monomers make contacts with identical half-sites.

As used herein, the term "pseudo-palindromic" refers to a recognition sequence consisting of inverted repeats of non-identical or imperfectly palindromic half-sites. In this case, the pseudo-palindromic sequence need not be palindromic with respect to the center sequence, and also can deviate from a perfectly palindromic sequence between the two half-sites. Pseudo-palindromic DNA sequences are typical of the natural DNA sites recognized by wild-type homodimeric meganucleases in which two identical enzyme monomers make contacts with different half-sites.

As used herein, the term "non-palindromic" refers to a recognition sequence composed of two unrelated half-sites of a meganuclease. In this case, the non-palindromic sequence need not be palindromic with respect to either the center sequence or the two monomer half-sites. Non-palindromic DNA sequences are recognized by either heterodimeric meganucleases or single-chain meganucleases comprising a pair of domains that recognize non-identical half-sites.

As used herein, the term "activity" refers to the rate at which a meganuclease of the invention cleaves a particular recognition sequence. Such activity is a measurable enzymatic reaction, involving the hydrolysis of phosphodiester bonds of double-stranded DNA. The activity of a meganuclease acting on a particular DNA substrate is affected by the affinity or avidity of the meganuclease for that particular DNA substrate which is, in turn, affected by both sequence-specific and non-sequence-specific interactions with the DNA.

As used herein, the term "homologous recombination" refers to the natural, cellular process in which a double-stranded DNA-break is repaired using a homologous DNA sequence as the repair template (see, e.g., Cahill et al. (2006), *Front. Biosci.* 11:1958-1976). The homologous DNA sequence may be an endogenous chromosomal sequence or an exogenous nucleic acid that was delivered to the cell. Thus, for some applications, a meganuclease is used to cleave a recognition sequence within a target sequence in a genome and an exogenous nucleic acid with homology to or substantial sequence similarity with the target sequence is delivered into the cell and used as a template for repair by homologous recombination. The DNA sequence of the exogenous nucleic acid, which may differ significantly from the target sequence, is thereby incorporated into the chromosomal sequence. The process of homologous recombination occurs primarily in eukaryotic organisms. The term "homology" is used herein as equivalent to "sequence similarity" and is not intended to require identity by descent or phylogenetic relatedness.

As used herein, the term "non-homologous end-joining" refers to the natural, cellular process in which a double-stranded DNA-break is repaired by the direct joining of two non-homologous DNA segments (see, e.g., Cahill et al. (2006), *Front. Biosci.* 11:1958-1976). DNA repair by non-homologous end joining is error-prone and frequently results in the untemplated addition or deletion of DNA sequences at the site of repair. Thus, for some applications, a meganuclease can be used to produce a double-stranded break at a meganuclease recognition sequence within a target sequence in a genome to disrupt a gene (e.g., by introducing base insertions, base deletions, or frameshift mutations) by non-homologous end joining. For other applications, an exogenous nucleic acid lacking homology to or substantial sequence similarity with the target sequence may be captured at the site of a meganuclease-stimulated double-stranded DNA break by non-homologous end joining (see, e.g., Salomon et al. (1998), *EMBO J.* 17:6086-6095). The process of non-homologous end joining occurs in both eukaryotes and prokaryotes such as bacteria.

As used herein, the term "sequence of interest" means any nucleic acid sequence, whether it codes for a protein, RNA, or regulatory element (e.g., an enhancer, silencer, or promoter sequence), that can be inserted into a genome or used to replace a genomic DNA sequence using a meganuclease protein. Sequences of interest can have heterologous DNA sequences that allow for tagging a protein or RNA that is expressed from the sequence of interest. For instance, a protein can be tagged with tags including, but not limited to, an epitope (e.g., c-myc, FLAG) or other ligand (e.g., poly-His). Furthermore, a sequence of interest can encode a fusion protein, according to techniques known in the art (see, e.g., Ausubel et al., *Current Protocols in Molecular Biology*, Wiley 1999). For some applications, the sequence of interest is flanked by a DNA sequence that is recognized by the meganuclease for cleavage. Thus, the flanking sequences are cleaved allowing for proper insertion of the sequence of interest into genomic recognition sequences cleaved by a meganuclease. For some applications, the entire sequence of interest is homologous to or has substantial sequence similarity with a target sequence in the genome such that homologous recombination effectively replaces the target sequence with the sequence of interest. For other applications, the sequence of interest is flanked by DNA sequences with homology to or substantial sequence similarity with the target sequence such that homologous recombination inserts the sequence of interest within the genome at the locus of the target sequence. For some applications, the sequence of interest is substantially identical to the target sequence except for mutations or other modifications in the meganuclease recognition sequence such that the meganuclease can not cleave the target sequence after it has been modified by the sequence of interest.

As used herein, the term "single-chain meganuclease" refers to a polypeptide comprising a pair of meganuclease subunits joined by a linker. A single-chain meganuclease has the organization: N-terminal subunit-Linker-C-terminal subunit. The two meganuclease subunits, each of which is derived from I-CreI, will generally be non-identical in amino acid sequence and will recognize non-identical half-sites. Thus, single-chain meganucleases typically cleave pseudo-palindromic or non-palindromic recognition sequences. A single chain meganuclease may be referred to as a "single-chain heterodimer" or "single-chain heterodimeric meganuclease" although it is not, in fact, dimeric.

As used herein, unless specifically indicated otherwise, the word "or" is used in the inclusive sense of "and/or" and not the exclusive sense of "either/or."

2.1 Preferred Center Sequences for I-CreI-Derived Meganucleases

The present invention is based, in part, in the identification of subsets of the possible four base pair center sequences that are preferred by I-CreI-derived meganucleases. As the wild-type enzyme does not make significant contacts with the bases in the center sequence, the same center sequence preferences of the wild-type I-CreI homing nuclease apply to rationally-designed I-CreI-derived meganucleases which have been redesigned with respect to, for example, half-site preference, DNA-binding affinity, and/or heterodimerization ability. This invention provides, therefore, important criteria that can be considered in determining whether or not a particular 22 base pair DNA sequence is a suitable I-CreI-derived meganuclease recognition sequence.

The preferred set of center sequences was determined using a genetically-engineered meganuclease called "DJ1" (SEQ ID NO: 4). The production of this meganuclease is described in WO 2007/047859. DJ1 is a homodimeric I-CreI-derived meganuclease which was designed to recognize a palindromic meganuclease recognition sequence (SEQ ID NO: 5, SEQ ID NO: 6) that differs at 4 positions per half-site relative to wild-type I-CreI. This change in half-site specificity was achieved by the introduction of 6 amino acid substitutions to wild type I-CreI (K28D, N30R, S32N, Q38E, S40R, and T42R).

To test for cleavage activity with respect to various recognition sequences, DJ1 was expressed in *E. coli* and purified as described in Example 1 of WO 2007/047859. Then, 25 picomoles of purified meganuclease protein were added to a 10 nM solution of plasmid DNA substrate in SA buffer (25 mM Tris-HCL, pH 8.0, 100 mM NaCl, 5 mM $MgCl_2$, 5 mM EDTA) in a 25 microliter reaction. 1 microliter of XmnI restriction enzyme was added to linearize the plasmid substrates. Reactions were incubated at 37° C. for 4 hours and were then visualized by gel electrophoresis to determine the extent to which each was cleaved by the DJ1 meganuclease.

Figure 2A:
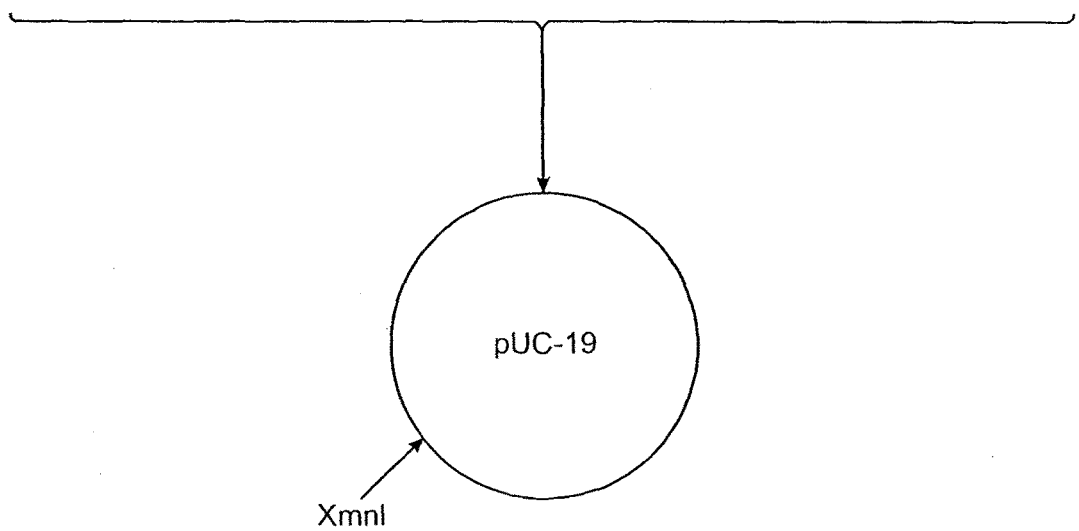
FIG. 2. (A) Schematic diagram of the plasmid substrates evaluated to determine center sequence preference (SEQ ID NOS 22-23, respectively, in order of appearance). A set of pUC-19 plasmids were produced which harbored potential recognition sequences for the genetically-engineered meganuclease DJ1. These potential recognition sequences comprised a pair of inverted DJ1 half-sites separated by a variety of different four base pair center sequences (numbered +1 through +4), as described below. (B) Example of gel electrophoresis data showing DJ1 meganuclease cleavage of plasmid substrates described in (A). The "uncut" arrow indicates XmnI linearized plasmid substrate. The "cut" arrows indicate XmnI linearized plasmid substrates which have also been successfully cleaved by DJ1.
Figure 2B:
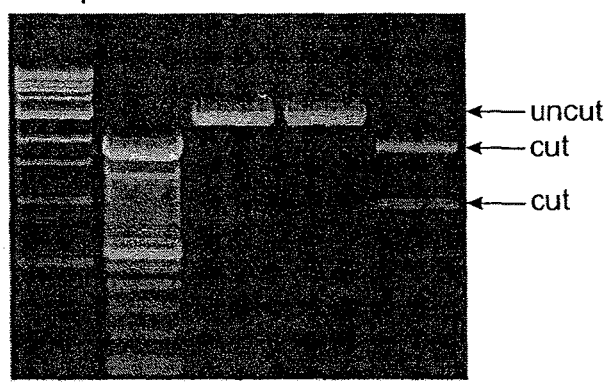

The plasmid substrates used in these experiments comprised a pUC-19 plasmid in which a potential meganuclease recognition sequence was inserted into the polylinker site (SmaI site). Each potential meganuclease recognition site comprised a pair of inverted DJ1 half-sites (SEQ ID NO: 7) separated by a different center sequence. Thus, by evaluating DJ1 cleavage of multiple DNA substrates differing only by center sequence, it was possible to determine which center sequences are the most amenable to meganuclease cleavage (FIG. 2).

Initially, only the influence of the $N_{+2}$ and $N_{+3}$ bases were evaluated. The X-ray crystal structure of I-CreI in complex with its natural DNA site shows that the DNA is distorted at these central two base pairs (Jurica et al. (1998), *Mol Cell.* 2:469-76). Computer modeling suggests that a purine (G or A) at $N_{+2}$ is incompatible with a pyrimidine (C or T) at $N_{+3}$. This is because the distortion introduced by I-CreI binding causes a steric clash between a purine base at $N_{+2}$ and a second purine base-paired to a pyrimidine at $N_{+3}$. This expected incompatibility was verified experimentally by incubating DJ1 protein with plasmid substrates harboring meganuclease recognition sites with all possible center sequences of the form $A_{+1}X_{+2}X_{+3}T_{+4}$ in which X is any base. The results are summarized in Table 1. For Tables 1-5, "Activity" refers to the following:

−: no cleavage in 4 hours
+: 1%-25% cleavage in 4 hours
++: 26%-75% cleavage in 4 hours
+++: 75%-100% cleavage in 4 hours

TABLE 1

The effect of changes at $N_{+2}$ and $N_{+3}$

| Seq. No. | $N_{+1}$ | $N_{+2}$ | $N_{+3}$ | $N_{+4}$ | Activity |
|---|---|---|---|---|---|
| 1 | A | A | A | T | + |
| 2 | A | A | C | T | − |
| 3 | A | A | G | T | + |
| 4 | A | A | T | T | − |
| 5 | A | C | A | T | + |
| 6 | A | C | C | T | + |
| 7 | A | C | G | T | + |
| 8 | A | C | T | T | + |
| 9 | A | G | A | T | + |
| 10 | A | G | C | T | − |
| 11 | A | G | G | T | + |
| 12 | A | G | T | T | − |
| 13 | A | T | A | T | ++ |
| 14 | A | T | C | T | + |
| 15 | A | T | G | T | ++ |
| 16 | A | T | T | T | + |

Consistent with the computer modeling, it was found that the four plasmid substrates with a purine base at $N_{+2}$ and a pyrimidine base at $N_{+3}$ (sequence numbers 2, 4, 10, and 12) were not cut efficiently by DJ1.

Next, a more comprehensive evaluation of center sequence preference was performed. There are $4^4$ or 256 possible center sequences. Of these, 25%, or 64, have a purine base at $N_{+2}$ and pyrimidine at $N_{+3}$ and, therefore, were eliminated as center sequences based on the experiment described above. Of the remaining 192, 92 are redundant because meganucleases are symmetric and recognize bases equally on both the sense and antisense strand. For example, the sequence $A_{+1}A_{+2}A_{+3}A_{+4}$ on the sense strand is recognized by the meganuclease as $T_{+1}T_{+2}T_{+3}T_{+4}$ on the antisense strand and, thus, $A_{+1}A_{+2}A_{+3}A_{+4}$ and $T_{+1}T_{+2}T_{+3}T_{+4}$ are functionally equivalent. Taking these redundancies into account, as well as the aforementioned $N_{+2}/N_{+3}$ conflicts, there were 100 possible center sequences remaining. To determine which of these were preferred by meganucleases, we produced 100 plasmid substrates harboring these 100 center sequences flanked by inverted recognition half-sites for the DJ1 meganuclease. DJ1 was then incubated with each of the 100 plasmids and cleavage activity was evaluated as described above. These results are summarized in Table 2.

TABLE 2

| | Cleavable Center Sequences | | | | |
|---|---|---|---|---|---|
| Seq. No. | $N_{+1}$ | $N_{+2}$ | $N_{+3}$ | $N_{+4}$ | Activity |
| 1 | T | T | T | T | + |
| 2 | T | T | G | T | ++ |
| 3 | T | T | C | T | + |
| 4 | T | T | A | T | ++ |
| 5 | T | G | G | T | + |
| 6 | T | G | A | T | + |
| 7 | T | C | T | T | ++ |
| 8 | T | C | G | T | ++ |
| 9 | T | C | C | T | + |
| 10 | T | C | A | T | ++ |
| 11 | T | A | G | T | + |
| 12 | T | A | A | T | + |
| 13 | G | T | T | T | ++ |
| 14 | G | T | G | T | +++ |
| 15 | G | T | C | T | ++ |
| 16 | G | T | A | T | +++ |
| 17 | G | G | G | T | + |
| 18 | G | G | A | T | ++ |
| 19 | G | A | G | T | ++ |
| 20 | G | A | A | T | ++ |
| 21 | C | T | T | T | + |
| 22 | C | T | G | T | + |
| 23 | C | T | C | T | + |
| 24 | C | T | A | T | + |
| 25 | C | G | G | T | + |
| 26 | C | G | A | T | + |
| 27 | C | C | T | T | + |
| 28 | C | C | G | T | + |
| 29 | C | C | C | T | + |
| 30 | C | C | A | T | + |
| 31 | C | A | G | T | + |
| 32 | C | A | A | T | + |
| 33 | A | T | T | T | + |
| 34 | A | T | G | T | ++ |
| 35 | A | T | C | T | + |
| 36 | A | G | G | T | + |
| 37 | A | C | T | T | + |
| 38 | T | T | T | G | + |
| 39 | T | T | G | G | + |
| 40 | T | T | C | G | + |
| 41 | T | T | A | G | +++ |
| 42 | T | G | G | G | + |
| 43 | T | G | A | G | + |
| 44 | T | C | T | G | + |
| 45 | T | C | G | G | + |
| 46 | T | C | C | G | + |

TABLE 2-continued

| | Cleavable Center Sequences | | | | |
|---|---|---|---|---|---|
| Seq. No. | $N_{+1}$ | $N_{+2}$ | $N_{+3}$ | $N_{+4}$ | Activity |
| 47 | T | C | A | G | + |
| 48 | T | A | G | G | + |
| 49 | T | A | A | G | + |
| 50 | G | T | T | G | + |
| 51 | G | T | G | G | + |
| 52 | G | T | C | G | + |
| 53 | G | T | A | G | +++ |
| 54 | G | G | G | G | + |
| 55 | G | G | A | G | + |
| 56 | G | A | G | G | + |
| 57 | G | A | A | G | + |
| 58 | C | T | T | G | + |
| 59 | C | T | G | G | + |
| 60 | C | T | C | G | + |
| 61 | C | G | G | G | + |
| 62 | C | C | T | G | + |
| 63 | T | T | T | C | ++ |
| 64 | T | T | C | C | ++ |
| 65 | T | T | A | C | +++ |
| 66 | T | G | A | C | ++ |
| 67 | T | C | T | C | +++ |
| 68 | T | C | C | C | + |
| 69 | T | C | A | C | +++ |
| 70 | T | A | A | C | ++ |
| 71 | G | T | T | C | ++ |
| 72 | G | T | C | C | +++ |
| 73 | T | T | T | A | + |
| 74 | T | T | G | A | + |
| 75 | T | T | C | A | + |
| 76 | T | G | G | A | + |
| 77 | T | C | T | A | + |
| 78 | A | T | A | T | ++ |
| 79 | A | C | G | T | + |
| 80 | C | T | A | G | + |
| 81 | C | C | G | G | + |
| 82 | G | T | A | C | +++ |
| 83 | T | C | G | A | ++ |
| 84 | T | T | A | A | ++ |
| 85 | T | C | G | C | +++ |
| 86 | A | A | G | C | +++ |
| 87 | G | A | G | C | +++ |
| 88 | G | C | G | C | +++ |
| 89 | G | G | G | C | ++ |
| 90 | G | T | G | C | +++ |
| 91 | T | A | G | C | +++ |
| 92 | T | G | G | C | + |
| 93 | T | T | G | C | +++ |
| 94 | A | C | G | C | ++ |
| 95 | A | G | G | C | + |
| 96 | A | T | G | C | +++ |
| 97 | C | A | G | C | + |
| 98 | C | C | G | C | ++ |
| 99 | C | G | G | C | + |
| 100 | C | T | G | C | ++ |

For clarity, each of the center sequences listed in Table 2 is equivalent to its opposite strand sequence due to the fact that the I-CreI meganuclease binds its recognition sequence as a symmetric homodimer. Thus, sequence no. 100 in Table 2, $C_{+1}T_{+2}G_{+3}C_{+4}$, is equivalent to its opposite strand sequence, $G_{+1}C_{+2}A_{+3}G_{+4}$. From these data, a general set of center sequence preference rules emerge. These rules, which are not meant to supersede Table 1 or Table 2, include:
1. Center sequences with a purine base at $N_{+2}$ and a pyrimidine base at $N_{+3}$ cut very poorly, if at all.
2. G is preferred at $N_{+1}$. This is equivalent to C at $N_{+4}$. All of the most preferred center sequences have G at $N_{+1}$ and/or C at $N_{+4}$.
3. C is preferred at $N_{+2}$. This is equivalent to G at $N_{+3}$.
4. There is a preference for center sequences with a pyrimidine base at $N_{+2}$ and a purine base at $N_{+3}$.
5. There is a preference for sequences with at least 1 A-T base pair in the center sequence.

Thus, in general, preferred center sequences have the form $G_+N_{+2}R_{+3}X_{+4}$ where Y is a pyrimidine (C or T), R is a purine (A or G), and X is any base (A, C, G, or T).

2.2 In Vitro Applications Using Preferred Center Sequences

Genetically-engineered meganucleases have numerous potential in vitro applications including restriction mapping and cloning. These applications are known in the art and are discussed in WO 2007/047859.

One advantage of using genetically-engineered meganucleases rather than conventional restriction enzymes for applications such as cloning is the possibility of cutting DNA to leave a wide range of different 3' overhangs ("sticky ends") that are compatible with, for example, the 3' overhangs produced by cleaving a particular vector of interest. Thus, there are occasions when it is desirable to cleave a meganuclease recognition sequence with a sub-optimal center sequence in order to create a desired overhang.

Because in vitro DNA cleavage conditions are, in general, less stringent than conditions in vivo, the use of sub-optimal center sequences may be acceptable for such applications. For example, relative to in vivo applications, in vitro digests using engineered meganucleases can be performed at a higher ratio of meganuclease to DNA, there is typically less non-specific (genomic) DNA competing for meganuclease, and solution conditions can be optimized to favor meganuclease cleavage (e.g., using SA buffer as described above). Thus, a larger number of center sequences are suitable for in vitro applications than for in vivo applications. All of the center sequences listed in Table 2 are suitable for in vitro applications, but preferred and most preferred center sequences for in vitro applications are listed in Table 3 and Table 4, respectively, with their opposite strand sequences.

TABLE 3

Preferred Center Sequences for in vitro Applications

| Seq. No. | $N_{+1}N_{+2}N_{+3}N_{+4}$ | Opposite Strand Sequence |
|---|---|---|
| 1 | TTGT | ACAA |
| 2 | TTAT | ATAA |
| 3 | TCTT | AAGA |
| 4 | TCGT | ACGA |
| 5 | TCAT | ATGA |
| 6 | GTTT | AAAC |
| 7 | GTCT | AGAC |
| 8 | GGAT | ATCC |
| 9 | GAGT | ACTC |
| 10 | GAAT | ATTC |
| 11 | ATGT | ACAT |
| 12 | TTTC | GAAA |
| 13 | TTCC | GGAA |
| 14 | TGAC | GTCA |
| 15 | TAAC | GTTA |

TABLE 3-continued

Preferred Center Sequences for in vitro Applications

| Seq. No. | $N_{+1}N_{+2}N_{+3}N_{+4}$ | Opposite Strand Sequence |
|---|---|---|
| 16 | GTTC | GAAC |
| 17 | ATAT | ATAT |
| 18 | TCGA | TCGA |
| 19 | TTAA | TTAA |
| 20 | GGGC | GCCC |
| 21 | ACGC | GCGT |
| 22 | CCGC | GCGG |
| 23 | CTGC | GCAG |

TABLE 4

Most Preferred Center Sequences for in vitro Applications

| Seq. No. | $N_1N_2N_3N_4$ | Opposite Strand Sequence |
|---|---|---|
| 1 | GTGT | ACAC |
| 2 | GTAT | ATAC |
| 3 | TTAG | CTAA |
| 4 | GTAG | CTAC |
| 5 | TTAC | GTAA |
| 6 | TCTC | GAGA |
| 7 | TCAC | GTGA |
| 8 | GTCC | GGAC |
| 9 | GTAC | GTAC |
| 10 | TCGC | GCGA |
| 11 | AAGC | GCTT |
| 12 | GAGC | GCTC |
| 13 | GCGC | GCGC |
| 14 | GTGC | GCAC |
| 15 | TAGC | GCTA |
| 16 | TTGC | GCAA |
| 17 | ATGC | GCAT |

Obviously, not every 22 base pair DNA sequence having a preferred or most preferred center sequence is capable of being a meganuclease recognition sequence in vitro. The sequence of the half-sites flanking the center sequence must also be amenable to meganuclease recognition and cleavage. Methods for engineering a meganuclease including I-CreI, to recognize a pre-determined half-site are known in the art (see, e.g., WO 2007/047859). Thus, a preferred I-CreI-derived meganuclease recognition sequence for in vitro applications will comprise: (1) a first 9 base pair half-site amenable to recognition by a meganuclease monomer (or a first domain of a single-chain meganuclease); (2) a preferred or most preferred center sequence from Table 2 or Table 3;

and (3) a second 9 base pair half-site amenable to recognition by a meganuclease monomer (or a second domain of a single-chain meganuclease) in the reverse orientation relative to the first half-site.

Thus, in one aspect, the invention provides methods for cleaving a double-stranded DNA in vitro by (a) identifying at least one potential recognition site for at least one I-CreI-derived meganuclease within the DNA, wherein the potential recognition site has a four base pair central sequence selected from the group of central sequences of Table 2; (b) identifying an I-CreI-derived meganuclease which recognizes that recognition site in the DNA; and (c) contacting the I-CreI-derived meganuclease with the DNA; whereby the I-CreI meganuclease cleaves the DNA.

In another aspect, the invention provides methods for cleaving a double-stranded DNA in vitro by (a) introducing into the DNA a recognition site for an I-CreI-derived meganuclease having a four base pair central sequence selected from the group consisting of central sequences of Table 2; and (b) contacting the I-CreI-derived meganuclease with the DNA; whereby the I-CreI-derived meganuclease cleaves the DNA.

In particular, in some embodiments, the DNA is selected from a PCR product; an artificial chromosome; genomic DNA isolated from bacteria, fungi, plants, or animal cells; and viral DNA.

In some embodiments, the DNA is present in a nucleic acid selected from a plasmid, a prophage and a chromosome.

In some of the foregoing embodiments, the four base pair DNA sequence is selected from Table 3. In other embodiments, the four base pair DNA sequence is selected from Table 4.

In some embodiments, the I-CreI-derived meganuclease can be specifically designed for use with the chosen recognition site in the method.

2.3 In Vivo Applications Using Preferred Center Sequences

Applications such as gene therapy, cell engineering, and plant engineering require meganuclease function inside of a living cell (for clarity, any intracellular application will be referred to as an "in vivo" application whether or not such cell is isolated or part of a multicellular organism). These applications are known in the art and are described in, e.g., WO 2007/047859. In vivo applications are significantly restricted relative to in vitro applications with regard to the center sequence. This is because intracellular conditions cannot be manipulated to any great extent to favor meganuclease activity and/or because vast amounts of genomic DNA compete for meganuclease binding. Thus, only meganuclease recognition sequences with optimal center sequences are preferred for in vivo applications. Such sequences are listed in Table 5 with their opposite strand sequences.

TABLE 5

Preferred Center Sequences for in vivo applications.

| Seq. No. | $N_1N_2N_3N_4$ | Opposite Strand Sequence |
|---|---|---|
| 1 | GTGT | ACAC |
| 2 | GTAT | ATAC |
| 3 | TTAG | CTAA |

TABLE 5-continued

Preferred Center Sequences for in vivo applications.

| Seq. No. | $N_1N_2N_3N_4$ | Opposite Strand Sequence |
|---|---|---|
| 4 | GTAG | CTAC |
| 5 | TTAC | GTAA |
| 6 | TCTC | GAGA |
| 7 | TCAC | GTGA |
| 8 | GTCC | GGAC |
| 9 | GTAC | GTAC |
| 10 | TCGC | GCGA |
| 11 | AAGC | GCTT |
| 12 | GAGC | GCTC |
| 13 | GCGC | GCGC |
| 14 | GTGC | GCAC |
| 15 | TAGC | GCTA |
| 16 | TTGC | GCAA |
| 17 | ATGC | GCAT |

Obviously, not every 22 base pair DNA sequence having a preferred center sequence is capable of being a meganuclease recognition sequence in vivo. The sequence of the half-sites flanking the center sequence must also be amenable to meganuclease recognition and cleavage. Methods for engineering a meganuclease, including I-CreI, to recognize a pre-determined half-site are known in the art (see, e.g., WO 2007/047859). Thus, a preferred in vivo meganuclease recognition sequence will comprise: (1) a first 9 base pair half-site amenable to recognition by a meganuclease monomer (or a first domain of a single-chain meganuclease); (2) a preferred center sequence from Table 5; and (3) a second 9 base pair half-site amenable to recognition by a meganuclease monomer (or a second domain of a single-chain meganuclease) in the reverse orientation relative to the first half-site.

Thus, in one aspect, the invention provides methods for cleaving a double-stranded DNA in vivo by (a) identifying at least one potential recognition site for at least one I-CreI-derived meganuclease within the DNA, wherein the potential recognition site has a four base pair central sequence selected from the group of central sequences of Table 2; (b) identifying an I-CreI-derived meganuclease which recognizes that recognition site in the DNA; and (c) contacting the I-CreI-derived meganuclease with the DNA; whereby the I-CreI-derived meganuclease cleaves the DNA.

In another aspect, the invention provides methods for cleaving a double-stranded DNA in vivo by (a) introducing into the DNA a recognition site for an I-CreI-derived meganuclease having a four base pair central sequence selected from the group consisting of central sequences of Table 2; and (b) contacting the I-CreI-derived meganuclease with the DNA; whereby the I-CreI-derived meganuclease cleaves the DNA.

In some embodiments, the DNA is present in a cell selected from a bacterial, fungal, plant and animal cell.

In some embodiments, the DNA is present in a nucleic acid selected from a plasmid, a prophage and a chromosome.

In some of the foregoing embodiments, the four base pair DNA sequence is selected from Table 3. In other embodiments, the four base pair DNA sequence is selected from Table 4.

In some embodiments, the I-CreI-derived meganuclease is specifically designed for use with the chosen recognition site in the methods of the invention.

In some of the foregoing embodiments, the method includes the additional step of rationally-designing the I-CreI-derived meganuclease to recognize the chosen recognition site. In some embodiments, the method further comprises producing the I-CreI-derived meganuclease.

In another aspect, the invention provides cells transformed with a nucleic acid including (a) a first 9 base pair DNA sequence which can be bound by an I-CreI-derived meganuclease monomer or by a first domain from a single-chain I-CreI-derived meganuclease; (b) a four base pair DNA sequence selected from Table 2; and (c) a second 9 base pair DNA sequence which can be bound by an I-CreI-derived meganuclease monomer or by a second domain from a single-chain I-CreI-derived meganuclease; wherein the second 9 base pair DNA sequence is in the reverse orientation relative to the first.

In another aspect, the invention provides a cell containing an exogenous nucleic acid sequence integrated into its genome, including, in order: (a) a first exogenous 9 base pair DNA sequence which can be bound by an I-CreI-derived meganuclease monomer or by a first domain from a single-chain I-CreI-derived meganuclease; (b) an exogenous four base pair DNA sequence selected from Table 2; and (c) a second exogenous 9 base pair DNA sequence which can be bound by an I-CreI-derived meganuclease monomer or by a second domain from a single-chain I-CreI-derived meganuclease; wherein the second 9 base pair DNA sequence is in the reverse orientation relative to the first.

In another aspect, the invention provides a cell containing an exogenous nucleic acid sequence integrated into its genome, including, in order: (a) a first exogenous 9 base pair DNA sequence which can be bound by an I-CreI-derived meganuclease monomer or by a first domain from a single-chain I-CreI-derived meganuclease; (b) an exogenous two base pair DNA sequence, wherein the two base pairs correspond to bases $N_{+1}$ and $N_{+2}$ of a four base pair DNA sequence selected from Table 2; (c) an exogenous DNA sequence comprising a coding sequence which is expressed in the cell; (d) an exogenous two base pair DNA sequence, wherein the two base pairs correspond to bases $N_{+3}$ and $N_{+4}$ of a four base pair DNA sequence selected from Table 2; and (e) a second exogenous 9 base pair DNA sequence which can be bound by the I-CreI-derived meganuclease monomer or by a second domain from the single-chain I-CreI-derived meganuclease; wherein the second 9 base pair DNA sequence is in the reverse orientation relative to the first.

In some embodiments, the nucleic acid is a plasmid. In other embodiments, the nucleic acid is an artificial chromosome. In other embodiments, the nucleic acid is integrated into the genomic DNA of the cell. In other embodiments, the nucleic acid is a viral nucleic acid.

In some embodiments, the cell is selected from the group a human cell, a non-human animal cell, a plant cell, a bacterial cell, and a fungal cell.

In some of the foregoing embodiments, the four base pair DNA sequence is selected from Table 3. In other embodiments, the four base pair DNA sequence is selected from Table 4.

In some embodiments, the I-CreI meganuclease is specifically designed for use with the chosen recognition site in the methods of the invention.

2.4 Methods of Conducting a Custom-Designed, I-CreI-Derived Meganuclease Business A meganuclease business can be conducted based on I-CreI-derived meganucleases. For example, such business can operate as following. The business received a DNA sequence into which a double-strand break is to be introduced by a rationally-designed I CreI-derived meganuclease. The business identifies in the DNA sequence at least one recognition site for a rationally-designed I CreI-derived meganuclease with altered specificity relative to I-CreI, wherein the recognition site is not cleaved by a naturally-occurring I-CreI, wherein the recognition site has a four base pair central sequence selected from the group consisting of TTGT, TTAT, TCTT, TCGT, TCAT, GTTT, GTCT, GGAT, GAGT, GAAT, ATGT, TTTC, TTCC, TGAC, TAAC, GTTC, ATAT, TCGA, TTAA, GGGC, ACGC, CCGC, CTGC, ACAA, ATAA, AAGA, ACGA, ATGA, AAAC, AGAC, ATCC, ACTC, ATTC, ACAT, GAAA, GGAA, GTCA, GTTA, GAAC, ATAT, TCGA, TTAA, GCCC, GCGT, GCGG and GCAG. The business then provides a rationally-designed meganuclease that cleaves the recognition site in the DNA.

Optionally, the business rationally-designs an I-CreI-derived meganuclease that cleaves the recognition site in the DNA. Optionally, the business produces the rationally-designed I-CreI-derived meganuclease.

2.5 Specifically Excluded Center Sequences

The center sequences GTAC, ACAC, and GTGA have previously been shown to be effective center sequences for in vitro and in vivo applications. These center sequences are specifically excluded from some aspects of the present invention. In addition, the center sequences TTGA and GAAA have previously been shown to be poor center sequences for in vivo applications (Arnould, et al. (2007). *J. Mol. Biol.* 371: 49-65).

EXAMPLES

This invention is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below. Examples 1 and 2 refer to engineered meganucleases cleaving optimized meganuclease recognition sites in vivo in a model plant system. Example 3 refers to an engineered meganuclease cleaving optimized meganuclease recognition sites in vitro.

Example 1

Cleavage of an Optimized Meganuclease Recognition Site by a Rationally-Designed, I-CreI-Derived Meganuclease Homodimer In Vivo An engineered meganuclease called BRP2 (SEQ ID NO: 8) was produced using the method disclosed in WO 2007/047859. This meganuclease is derived from I-CreI and was engineered to recognize DNA sites that are not recognized by wild-type I-CreI (e.g., BRP2 recognition sequences include SEQ ID NO: 9 and SEQ ID NO: 10, or SEQ ID NO: 11 and SEQ ID NO: 12). To facilitate nuclear localization of the engineered meganuclease, an SV40 nuclear localization signal (NLS, SEQ ID NO: 13) was added to the N-terminus of the protein. Conventional *Agrobacterium*-mediated transformation procedures were used to transform *Arabidopsis thaliana* with a T-DNA containing a codon-optimized BRP2 coding sequence (SEQ ID NO: 14). Expression of BRP2 meganuclease was under the control of a Hsp70 promoter and a NOS terminator. A pair of BRP2 recognition sequences were housed on the same T-DNA separated by 7 base pairs containing a PstI restriction enzyme site (FIG. 3a). BRP2 cutting of the pair of BRP2 recognition sequences in this construct was expected to excise the region between the recognition sequences and thereby remove the PstI restriction site (FIG. 3b). Two such T-DNA constructs were produced which varied the center sequence of the meganuclease recognition sequences flanking the PstI restriction enzyme site (FIG. 3c). In the first construct (the "GTAC construct"), the meganuclease recognition sites had the center sequence GTAC (a preferred in vivo center sequence, Table 5, sequence 9; SEQ ID NO: 9 and SEQ ID NO 10). The second construct (the "TAGA construct") had the center sequence TAGA (a non-preferred center sequence, opposite strand sequence to Table 2, sequence 77; SEQ ID NO: 11 and SEQ ID NO 12).

Stably transformed *Arabidopsis* plants carrying each construct were produced by selection for a kanamycin resistance marker housed on the T-DNA. Genomic DNA was then isolated from the transformed plants (by leaf punch) before and after heat-shock to induce BRP2 meganuclease expression. Genomic DNA samples were added to PCR reactions using primers to amplify the region of the T-DNA housing the meganuclease recognition sequences. PCR products were then digested with PstI and visualized by gel electrophoresis (FIG. 3d). Results are summarized in Table 6. Any PCR sample in which a significant percentage (>25%) of product was found to be resistant to PstI was considered to be indicative of in vivo meganuclease cleavage in that particular plant and was scored as "cut" in Table 6. It was found that, prior to heat-shock, the vast majority of PCR samples from plants carrying either construct retained the PstI site. After heat-shock, however, a large percentage of samples taken from plants transformed with the GTAC construct, but not the TAGA construct, had lost the PstI site. PCR products from the GTAC construct-transformed plants lacking a PstI site were cloned into a pUC-19 plasmid and sequenced. 100% of sequenced clones had a precise deletion of the region between the two BRP2 cut sites (as diagrammed in FIG. 3b). These results indicate that an engineered meganuclease is able to cleave a meganuclease recognition site in vivo provided it has an optimized center sequence.

TABLE 6

In vivo cleavage of optimized meganuclease recognition sequences by an engineered meganuclease homodimer.

| Construct | Before heat-shock | | After heat-shock | |
|---|---|---|---|---|
| | Cut | Uncut | Cut | Uncut |
| GTAC | 0 | 4 | 3 | 1 |
| TAGA | 0 | 22 | 0 | 22 |

Example 2

Cleavage of an Optimized Meganuclease Recognition Site by a Rationally-Designed, I-CreI-Derived Meganuclease Single-Chain Heterodimer In Vivo The engineered meganuclease BRP12-SC (SEQ ID NO: 15) was produced in accordance with WO 2007/047859, except that this meganuclease is a single-chain heterodimer. As discussed in WO 2007/047859, wild-type I-CreI binds to and cleaves DNA as a homodimer. As a consequence, the natural recognition sequence for I-CreI is pseudo-palindromic. The BRP12-SC recognition sequences, however, are non-palindromic (e.g., SEQ ID NO: 16 and SEQ ID NO: 17, or SEQ ID NO: 18 and SEQ ID NO: 19). This necessitates the use of an engineered meganuclease heterodimer comprising a pair of subunits each of which recognizes one half-site within the full-length recognition sequence. In the case of BRP12-SC, the two engineered meganuclease monomers are physically linked to one another using an amino acid linker to produce a single-chain heterodimer. This linker comprises amino acids 166-204 (SEQ ID NO: 20) of BRP12-SC. The linker sequence joins an N-terminal meganuclease subunit terminated at L165 (corresponding to L155 of wild-type I-CreI) with a C-terminal meganuclease subunit starting at K204 (corresponding to K7 of wild-type I-CreI). The benefits of physically linking the two meganuclease monomers using this novel linker is twofold: First, it ensures that the meganuclease monomers can only associate with one another (heterodimerize) to cut the non-palindromic BRP12-SC recognition sequence rather than also forming homodimers which can recognize palindromic or pseudopalindromic DNA sites that differ from the BRP12-SC recognition sequence. Second, the physical linking of meganuclease monomers obviates the need to express two monomers simultaneously in the same cell to obtain the desired heterodimer. This significantly simplifies vector construction in that it only requires a single gene expression cassette. As was the case with the BRP2 meganuclease discussed in Example 1, the BRP12-SC meganuclease has an SV40 nuclear localization signal (SEQ ID NO: 13) at its N-terminus.

Figures 4A, 4B:
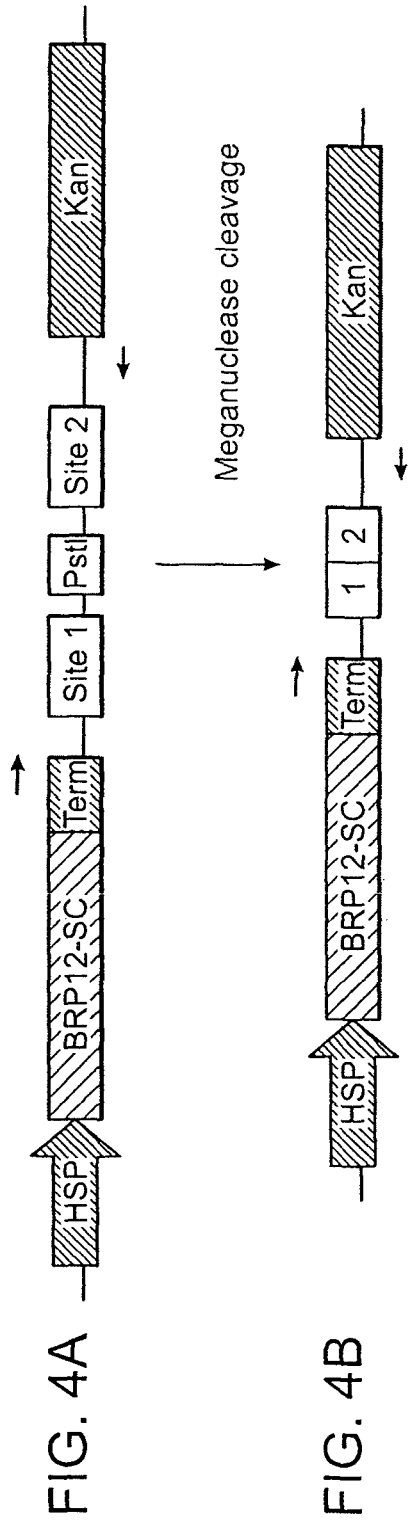
FIG. 4. (A) Schematic diagram of a T-DNA that was stably integrated into the *Arabidopsis thaliana* genome as described in Example 2. In this T-DNA construct, a codon-optimized gene encoding the BRP12-SC meganuclease (BRP12-SC) (SEQ ID NO: 15) is under the control of a Hsp70 promoter (HSP) and a NOS terminator (TERM). A pair of potential BRP12-SC recognition sequences (Site1, Site2) are housed adjacent to the terminator separated by 7 base, pairs containing a PstI restriction enzyme site (PstI). A kanamycin resistance marker (Kan) is also housed on the T-DNA to allow selection for stable transformants. (B) The expected product following BRP12-SC meganuclease cleavage of Site1 and Site2 showing loss of the intervening 7 base pair fragment and PstI restriction site. Arrows show the location of PCR primers used to screen for cleavage of the T-DNA. (C) Sequences of the BRP12-SC recognition sequences housed on either the GTAC construct (SEQ ID NO: 16) (GTAC) or the TAGA construct (SEQ ID NO: 18) (TAGA) with center sequences underlined.

Conventional *Agrobacterium*-mediated transformation procedures were used to transform *Arabidopsis thaliana* with a T-DNA containing a codon-optimized BRP12-SC coding sequence (SEQ ID NO: 21). Expression of BRP12-SC meganuclease was under the control of a Hsp70 promoter and a NOS terminator. A pair of BRP12-SC recognition sequences were housed on the same T-DNA separated by 7 base pairs containing a PstI restriction enzyme site (FIG. 4a). BRP12-SC cutting of the pair of BRP12-SC recognition sequences in this construct was expected to excise the region between the recognition sequences and thereby remove the PstI restriction site (FIG. 4b). Two such T-DNA constructs were produced which varied only in the center sequences of the meganuclease recognition sequences flanking the PstI restriction enzyme site (FIG. 4c). In the first construct (the "GTAC construct"), the meganuclease recognition sites had the center sequence GTAC (a preferred in vivo center sequence, Table 5, sequence 9; SEQ ID NO: 16 and SEQ ID NO 17). The second construct (the "TAGA construct") had the center sequence TAGA (a non-preferred center sequence, opposite strand sequence to Table 2, sequence 77; SEQ ID NO: 18 and SEQ ID NO 19).

Stably transformed *Arabidopsis* plants carrying each construct were produced by selection for a kanamycin resistance marker housed on the T-DNA. Genomic DNA was then isolated from the transformed plants (by leaf punch) before and after heat-shock to induce BRP12-SC meganuclease expression. Genomic DNA samples were added to PCR reactions using primers to amplify the region of the T-DNA housing the meganuclease recognition sequences. PCR products were then digested with PstI and visualized by gel electrophoresis. The results of this analysis are presented in Table 7. Any PCR sample in which a significant percentage (>25%) of product was found to be resistant to PstI was considered to be indicative of in vivo meganuclease cleavage and was scored as "cut" in Table 7. It was found that, prior to heat-shock, the vast majority of PCR samples from plants carrying either construct retained the PstI site. After heat-shock, however, a large percentage of samples taken from plants transformed with the GTAC construct, but not the TAGA construct, had lost the PstI site. PCR products from the GTAC construct-transformed plants lacking a PstI site were cloned into a pUC-19 plasmid and sequenced. 100% of sequenced clones had a precise deletion of the region between the two BRP12-SC cut sites (as diagrammed in FIG. 4b). These results indicate that an engineered single chain meganuclease is able to cleave a meganuclease recognition site in vivo provided it has an optimized center sequence.

TABLE 7

In vivo cleavage of optimized meganuclease recognition sequences by an engineered meganuclease homodimer.

| Construct | Before heat-shock | | After heat-shock | |
|---|---|---|---|---|
| | Cut | Uncut | Cut | Uncut |
| GTAC | 0 | 23 | 8 | 15 |
| TAGA | 0 | 59 | 1 | 58 |

Example 3

Figure 5:
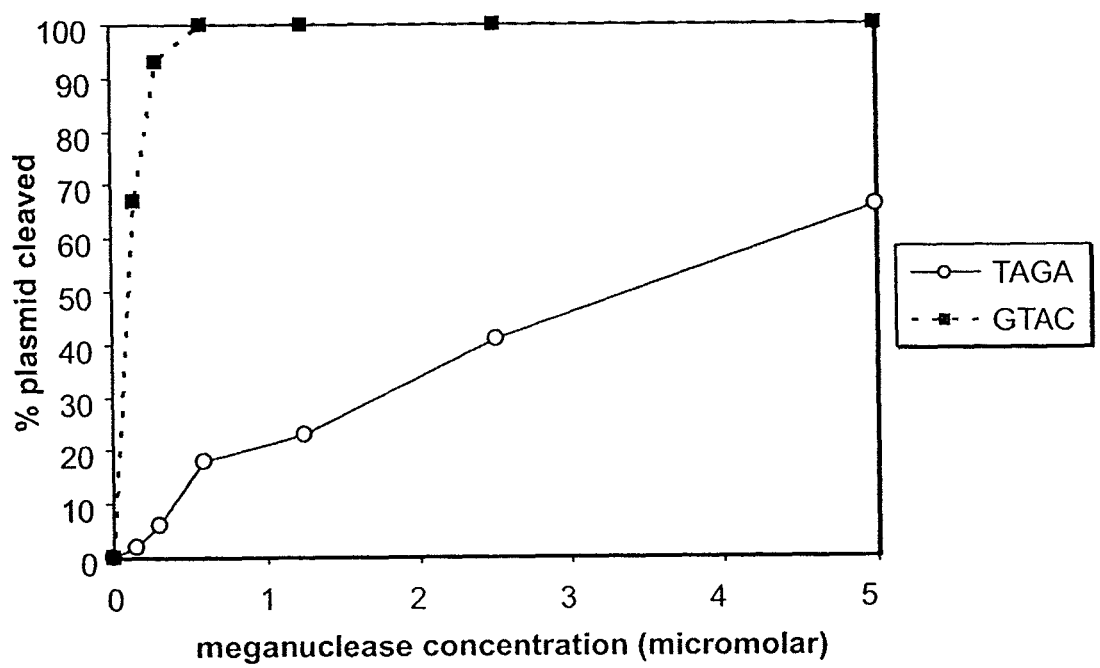
FIG. 5. Graphic representation of the effects of meganuclease concentration and center sequence on in vitro meganuclease cleavage. The BRP2 meganuclease (SEQ ID NO: 8, see Example 1) was added at the indicated concentration to a digest reaction containing 0.25 picomoles of a plasmid substrate harboring either a BRP2 recognition sequence with the center sequence GTAC or a BRP2 recognition sequence with the center sequence TAGA. Reactions were 25 microliters in SA buffer (25 mM Tris-HCL, pH 8.0, 100 mM NaCl, 5 mM $MgCl_2$, 5 mM EDTA). Reactions were incubated at 37° C. for 2 hours and were then visualized by gel electrophoresis and the percent of plasmid substrate cleaved by the meganuclease was plotted as a function of meganuclease concentration.

Cleavage of an Optimized Meganuclease Recognition Site by a Rationally-Designed, I-CreI-Derived Meganuclease Homodimer In Vitro The BRP2 meganuclease described in Example 1 (SEQ ID NO: 8) was expressed in *E. coli* and purified as in Example 1 of WO 2007/047859. The purified meganuclease was then added at varying concentrations to reactions containing plasmids harboring BRP2 recognition sequences with either a GTAC or TAGA center sequence (0.25 picomoles of plasmid substrate in 25 microliters of SA buffer: 25 mM Tris-HCL, pH 8.0, 100 mM NaCl, 5 mM MgCl$_2$, 5 mM EDTA). Reactions were incubated at 37° C. for 2 hours and were then visualized by gel electrophoresis and the percentage of each plasmid substrate cleaved by the meganuclease was plotted as a function of meganuclease concentration (FIG. 5). It was found that the plasmid substrate with the TAGA center sequence was cleaved by the meganuclease in vitro, but that cleavage of this substrate required a far higher concentration of BRP2 meganuclease than did cleavage of the GTAC substrate.

SEQUENCE LISTING

```
SEQ ID NO: 1 (wild-type I-CreI, Genbank Accession #P05725)
   1    MNTKYNKEFL LYLAGFVDGD GSIIAQIKPN QSYKFKHQLS LAFQVTQKTQ RRWFLDKLVD

61    EIGVGYVRDR GSVSDYILSE IKPLHNFLTQ LQPFLKLKQK QANLVLKIIW RLPSAKESPD

121    KFLEVCTWVD QIAALNDSKT RKTTSETVRA VLDSLSEKKK SSP

SEQ ID NO: 2 (wild-type I-CreI recognition sequence)
   1    GAAACTGTCT CACGACGTTT TG SEQ ID NO: 3 (wild-type I-CreI recognition sequence)
   1    CAAAACGTCG TGAGACAGTT TC SEQ ID NO: 4 (DJ1 amino acid sequence)
   1    MNTKYNKEFL LYLAGFVDGD GSIIAQIDPR QNYKFKHELR LRFQVTQKTQ RRWFLDKLVD

61    EIGVGYVRDR GSVSDYILSE IKPLHNFLTQ LQPFLKLKQK QANLVLKIIE QLPSAKESPD

121    KFLEVCTWVD QIAALNDSKT RKTTSETVRA VLDSLSEKKK SSP

SEQ ID NO: 5 (DJ1 recognition sequence-GTGA center sequence)
   1    AACGGTGTCG TGAGACACCG TT SEQ ID NO: 6 (DJ1 recognition sequence-GTGA center sequence)
   1    AACGGTGTCT CACGACACCG TT SEQ ID NO: 7 (DJ1 half-site)
   1    AACGGTGTC SEQ ID NO: 8 (BRP2 amino acid sequence)
   1    MGPKKKRKVI MNTKYNKEFL LYLAGFVDGD GSIIASIRPR QSCKFKHELE

51    LRFQVTQKTQ RRWFLDKLVD EIGVGYVRDR GSVSDYRLSQ IKPLHNFLTQ
```

```
     101     LQPFLKLKQK QANLVLKIIE QLPSAKESPD KFLEVCTWVD QIAALNDSKT

151     RKTTSETVRA VLDSLSEKKK SSP

SEQ ID NO: 9 (BRP2 recognition sequence-GTAC center sequence)
       1     CTCCGGGTCG TACGACCCGG AG SEQ ID NO: 10 (BRP2 recognition sequence-GTAC center sequence)
       1     CTCCGGGTCG TACGACCCGG AG SEQ ID NO: 11 (BRP2 recognition sequence-TAGA center sequence)
       1     CTCCGGGTCT AGAGACCCGG AG SEQ ID NO: 12 (BRP2 recognition sequence-TAGA center sequence)
       1     CTCCGGGTCT CTAGACCCGG AG SEQ ID NO: 13 (SV40 nuclear localization signal amino acid sequence)
       1     MAPKKKRKV SEQ ID NO: 14 (BRP2 codon-optimized DNA sequence)
       1     ATGGGCCCGA GAAGAAGCG CAAGGTCATC ATGAACACCA AGTACAACAA

51     GGAGTTCCTG CTCTACCTGG CGGGCTTCGT GGACGGGGAC GGCTCCATCA

101     TCGCCTCCAT CCGCCCGCGT CAGTCCTGCA AGTTCAAGCA TGAGCTGGAA

151     CTCCGGTTCC AGGTCACGCA GAAGACACAG CGCCGTTGGT TCCTCGACAA

201     GCTGGTGGAC GAGATCGGGG TGGGCTACGT GCGCGACCGC GGCAGCGTCT

251     CCGACTACCG CCTGAGCCAG ATCAAGCCTC TGCACAACTT CCTGACCCAG

301     CTCCAGCCCT TCCTGAAGCT CAAGCAGAAG CAGGCCAACC TCGTGCTGAA

351     GATCATCGAG CAGCTGCCCT CCGCCAAGGA ATCCCCGGAC AAGTTCCTGG

401     AGGTGTGCAC CTGGGTGGAC CAGATCGCCG CTCTGAACGA CTCCAAGACC

451     CGCAAGACCA CTTCCGAGAC CGTCCGCGCC GTGCTGGACA GTCTCTCCGA

501     GAAGAAGAAG TCGTCCCCCT AG

SEQ ID NO: 15 (BRP12-SC amino acid sequence)
       1     MGPKKKRKVI MNTKYNKEFL LYLAGFVDGD GSIKAQIRPR QSRKFKHELE

51     LTFQVTQKTQ RRWFLDKLVD EIGVGKVYDR GSVSDYELSQ IKPLHNFLTQ

101     LQPFLKLKQK QANLVLKIIE QLPSAKESPD KFLEVCTWVD QIAALNDSKT

151     RKTTSETVRA VLDSLPGSVG GLSPSQASSA ASSASSSPGS GISEALRAGA

201     TKSKEFLLYL AGFVDGDGSI IASIRPRQSC KFKHELELRF QVTQKTQRRW

251     FLDKLVDEIG VGYVRDRGSV SDYRLSQIKP LHNFLTQLQP FLKLKQKQAN

301     LVLKIIEQLP SAKESPDKFL EVCTWVDQIA ALNDSKTRKT TSETVRAVLD

351     SLSEKKKSSP

SEQ ID NO: 16 (BRP12-SC recognition sequence-GTAC center sequence)
       1     TGCCTCCTCG TACGACCCGG AG SEQ ID NO: 17 (BRP12-SC recognition sequence-GTAC center sequence)
       1     CTCCGGGTCG TACGAGGAGG CA SEQ ID NO: 18 (BRP12-SC recognition sequence-TAGA center sequence)
       1     TGCCTCCTCT AGAGACCCGG AG SEQ ID NO: 19 (BRP12-SC recognition sequence-TAGA center sequence)
       1     CTCCGGGTCT CTAGAGGAGG CA SEQ ID NO: 20 (BRP12-SC linker amino acid sequence)
       1     PGSVGGLSPS QASSAASSAS SSPGSGISEA LRAGATKS
```

SEQUENCE LISTING

SEQ ID NO: 21 (BRP12-SC codon-optimized DNA sequence)
```
   1   ATGGGCCCGA AGAAGAAGCG CAAGGTCATC ATGAACACCA AGTACAACAA
  51   GGAGTTCCTG CTCTACCTGG CCGGCTTCGT GGACGGCGAC GGCTCCATCA
 101   AGGCGCAGAT CCGTCCGCGG CAGAGCCGGA AGTTCAAGCA CGAGCTCGAG
 151   CTGACCTTCC AGGTGACCCA GAAGACGCAG AGGCGCTGGT TCCTCGACAA
 201   GCTGGTGGAC GAGATCGGGG TGGGCAAGGT CTACGACCGC GGGTCGGTGT
 251   CCGACTACGA GCTCTCCCAG ATCAAGCCCC TGCACAACTT CCTCACCCAG
 301   CTCCAGCCGT TCCTGAAGCT CAAGCAGAAG CAGGCCAACC TCGTGCTGAA
 351   GATCATCGAG CAGCTGCCCT CCGCCAAGGA ATCCCCGGAC AAGTTCCTGG
 401   AGGTGTGCAC GTGGGTGGAC CAGATCGCGG CCCTCAACGA CAGCAAGACC
 451   CGCAAGACGA CCTCGGAGAC GGTGCGGGCG GTCCTGGACT CCCTCCCAGG
 501   ATCCGTGGGA GGTCTATCGC CATCTCAGGC ATCCAGCGCC GCATCCTCGG
 551   CTTCCTCAAG CCCGGGTTCA GGGATCTCCG AAGCACTCAG AGCTGGAGCA
 601   ACTAAGTCCA AGGAATTCCT GCTCTACCTG GCGGGCTTCG TGGACGGGGA
 651   CGGCTCCATC ATCGCCTCCA TCCGCCCGCG TCAGTCCTGC AAGTTCAAGC
 701   ATGAGCTGGA ACTCCGGTTC AGGTCACGAG AGAAGACACA GCGCCGTTGG
 751   TTCCTCGACA AGCTGGTGGA CGAGATCGGG GTGGGCTACG TGCGCGACCG
 801   CGGCAGCGTC TCCGACTACC GCCTGAGCCA GATCAAGCCT CTGCACAACT
 851   TCCTGACCCA GCTCCAGCCC TTCCTGAAGC TCAAGCAGAA GCAGGCCAAC
 901   CTCGTGCTGA AGATCATCGA GCAGCTGCCC TCCGCCAAGG AATCCCCGGA
 951   CAAGTTCCTG GAGGTGTGCA CCTGGGTGGA CCAGATCGCC GCTCTGAACG
1001   ACTCCAAGAC CCGCAAGACC ACTTCCGAGA CCGTCCGCGC CGTGCTGGAC
1051   AGTCTCTCCG AGAAGAAGAA GTCGTCCCCC TAG
```

SEQ ID NO: 22 (recognition sequence)
```
   1   aacggtgton nnngacaccg tt
```

SEQ ID NO: 23 (recognition sequence)
```
   1   aacggtgton nnngacaccg tt
```

SEQ ID NO: 24 ("LAGLIDADG" family motif peptide)
```
   1   LAGLIDADG
```

The invention claimed is:

1. A method for cleaving a double-stranded DNA comprising:
   (a) identifying in said DNA at least one recognition site for a rationally-designed I-CreI-derived meganuclease with altered specificity relative to I-CreI, wherein said recognition site is not cleaved by a naturally-occurring I-CreI,
   wherein said recognition site has a four base pair central sequence selected from the group consisting of GTAT and ATGC;
   (b) providing said rationally-designed meganuclease; and
   (c) contacting said DNA with said rationally-designed meganuclease;
   whereby said rationally-designed meganuclease cleaves said DNA.

2. The method of claim 1, wherein said DNA cleavage is in vitro.

3. The method of claim 1, wherein said DNA is selected from the group consisting of a PCR product; an artificial chromosome; genomic DNA isolated from bacteria, fungi, plants, or animal cells; and viral DNA.

4. The method of claim 1, wherein said DNA cleavage is in vivo.

5. The method of claim 4, wherein said DNA is present in a cell selected from the group consisting of a bacterial, fungal, plant and animal cell.

6. The method of claim 4, wherein said DNA is present in a nucleic acid selected from the group consisting of a plasmid, a prophage and a chromosome.

7. The method of claim 1, further comprising rationally-designing said I-CreI-derived meganuclease to recognize said recognition site.

8. The method of claim 1, further comprising producing said rationally-designed I-CreI-derived meganuclease.

9. The method of claim 1, wherein said recognition site has a four base pair central sequence consisting of GTAT.

10. The method of claim 1 wherein said recognition site has a four base pair central sequence consisting of ATGC.

* * * * *